United States Patent
Weichenberger et al.

(10) Patent No.: US 11,464,494 B2
(45) Date of Patent: Oct. 11, 2022

(54) METHOD AND SYSTEM TO REVERT A DEPOLING EFFECT EXHIBITED BY AN ULTRASOUND TRANSDUCER

(71) Applicant: GE Precision Healthcare LLC, Wauwatosa, WI (US)

(72) Inventors: Harald Weichenberger, Oberhofen (AT); Reinhold Brüstle, Frankenburg (AT); Anton Hörl, Strasswalchen (AT); Bruno Hans Haider, Rehoboth Beach, DE (US); Rene Hechtfischer, Zell am Moos (AT)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 240 days.

(21) Appl. No.: 16/799,190

(22) Filed: Feb. 24, 2020

(65) Prior Publication Data
US 2021/0015466 A1 Jan. 21, 2021

Related U.S. Application Data

(63) Continuation-in-part of application No. 16/516,798, filed on Jul. 19, 2019.

(51) Int. Cl.
*A61B 8/08* (2006.01)
*A61B 8/00* (2006.01)
*G01S 7/52* (2006.01)

(52) U.S. Cl.
CPC .......... *A61B 8/5269* (2013.01); *A61B 8/4494* (2013.01); *G01S 7/52046* (2013.01)

(58) Field of Classification Search
CPC .. A61B 8/5269; A61B 8/4494; G01S 7/52046
See application file for complete search history.

(56) References Cited

U.S. PATENT DOCUMENTS

| 2,166,763 A | 7/1939 | Mason |
| 4,670,682 A | 6/1987 | Harnden, Jr. et al. |
| 5,295,487 A | 3/1994 | Saitoh et al. |

(Continued)

FOREIGN PATENT DOCUMENTS

| EP | 3586979 A1 | 1/2020 |
| JP | 2012139460 A | 7/2012 |
| WO | 2017002007 A1 | 1/2017 |

*Primary Examiner* — Isam A Alsomiri
*Assistant Examiner* — Abdallah Abulaban
(74) *Attorney, Agent, or Firm* — The Small Patent Law Group LLC; Dean D. Small

(57) ABSTRACT

An ultrasound system, probe and method are provided that comprise a transducer with piezoelectric transducer elements polarized in a poling direction, wherein over time one or more of the transducer elements possibly exhibit a depoling effect; and one or more drive circuits configured to: i) generate a transmit signal having at least first polarity segments, the first segments having corresponding first peak amplitudes; ii) generate a repoling signal having a repoling pattern configured to at least partially revert the depoling effect exhibited by the one or more transducer elements; and iii) generate a bias signal in the poling direction, the bias signal combined with the at least one of the transmit signal or the repoling signal to form a corresponding at least one of a biased transmit signal or a bias repoling signal, that is shifted in the poling direction.

20 Claims, 19 Drawing Sheets

(56) References Cited

U.S. PATENT DOCUMENTS

| | | | |
|---|---|---|---|
| 5,298,828 A | 3/1994 | Radovanovich | |
| 5,402,791 A | 4/1995 | Saitoh et al. | |
| 5,438,998 A | 8/1995 | Hanafy | |
| 5,740,128 A | 4/1998 | Hossack et al. | |
| 5,833,613 A | 11/1998 | Averkiou et al. | |
| 5,879,303 A | 3/1999 | Averkiou et al. | |
| 5,913,823 A | 6/1999 | Hedberg et al. | |
| 5,998,910 A | 12/1999 | Park et al. | |
| 6,238,481 B1 | 5/2001 | Yamashita et al. | |
| 6,241,676 B1 | 6/2001 | Savord | |
| 6,497,660 B1 * | 12/2002 | Dillman | G01S 7/5202 600/443 |
| 6,532,819 B1 | 3/2003 | Chen et al. | |
| 6,666,825 B2 | 12/2003 | Smith et al. | |
| 7,078,073 B2 | 7/2006 | Riigney et al. | |
| 7,094,444 B2 | 8/2006 | Rigney et al. | |
| 7,289,336 B2 | 10/2007 | Burdick, Jr. et al. | |
| 7,545,012 B2 | 6/2009 | Smith et al. | |
| 7,621,028 B2 | 11/2009 | Gelly et al. | |
| 8,659,212 B2 | 2/2014 | Eggen et al. | |
| 8,978,216 B2 | 3/2015 | Calisti et al. | |
| 9,966,578 B2 | 5/2018 | Stringer et al. | |
| 2004/0260181 A1 * | 12/2004 | Makita | H01L 41/257 600/459 |
| 2005/0215909 A1 * | 9/2005 | Barnes | G01S 7/52039 600/459 |
| 2018/0156904 A1 * | 6/2018 | Owen | A61B 8/4488 |

\* cited by examiner

METHOD AND SYSTEM TO REVERT A DEPOLING EFFECT EXHIBITED BY AN ULTRASOUND TRANSDUCER

RELATED APPLICATIONS

This application is a continuation-in-part of and claims priority to U.S. patent application Ser. No. 16/516,798, entitled "METHOD AND SYSTEM TO PREVENT DEPOLING OF ULTRASOUND TRANSDUCER," and filed Jul. 19, 2019, the entire subject matter of which is hereby incorporated by reference in its entirety.

FIELD

Aspects of the present disclosure relate to medical imaging. More specifically, certain embodiments relate to methods and systems for preventing depoling of an ultrasound transducer and for reverting a depoling effect when experienced.

BACKGROUND OF THE INVENTION

Single crystal piezoelectric materials may be used to form the acoustical stacks in ultrasound probes. The manufacture of an acoustical stack for use within an ultrasound probe includes stacking or sandwiching the piezoelectric material with other layers of materials such as graphite based materials or heavily loaded epoxy materials that may be used to form matching layers, flex materials with embedded copper traces, and/or other very hard material(s). During manufacture, ultrasound transducers are "poled" to improve the piezoelectric effect. The poling process is done by applying an electric field to the transducer along a predetermined direction relative to a reference axis of the piezoelectric material. The single crystal material and other transducer layers are diced into sub-parts which define separate transducer elements. The transducer elements are attached with electrodes during the assembly process. The electrodes are used to convey transmit signals to the corresponding transducer elements within the piezoelectric material and to collect received signals from the corresponding transducer elements.

During operation, a transmit voltage is applied between the electrodes connected to the piezoelectric material in order to induce an electric field in the transducer. The electric field results in a mechanical dimension change of the transducer element based on the piezoelectric effect. The mechanical dimension change is used to create an acoustic wave which is emitted by the probe. The acoustic wave is partially reflected on different anatomical layers. The reflected wave causes mechanical distortions of transducer elements, during a receive operation. The mechanical distortions during the receive operation induce an electrical signal, due to the piezoelectric effect, within the transducer. The electrodes transfer the electrical signals to the ultrasound console, where the electrical signals are used to create the ultrasound image. Transmit and receive operations are applied to a large number of electrodes and an associated large number of transducer elements.

If unduly high voltages are applied in a direction opposite to the initial poling direction the piezoelectric effect can be degraded. A degradation of this effect leads to lowered sensitivity of the ultrasound probe (also referred to as a depoling effect). The amount of degradation depends on many factors like transducer temperature, pattern of applied voltage signal, ending voltage polarity (positive or negative voltage), material composition of transducer, thickness of transducer et cetera. The depoling effect is a major challenge with single crystal ultrasound probes.

Heretofore, methods have been proposed to attempt to reduce the depoling effect. For example, U.S. Pat. No. 6,497,660, to Dillman et al., proposed to add a large biasing voltage to the transmit voltage signal. Dillman teaches to bias the bipolar voltage signal to maintain a same polarity as the poling direction of the transducer throughout a transmit operation. During the transmit cycle, Dillman's bias generator shifts the bipolar voltage signal such that instead of sitting at 0 Volts in the quiescent state, the bipolar voltage signal sits at least −XV volts. In FIG. 4 Dillman shows a biased bipolar voltage signal that has a quiescent state at −Xv, a peak value of 0 volts and a minimum value of −2XV, such that the biased bipolar voltage signal preferably should not cross 0 Volts. However, in order to maintain Dillman's large biasing voltage, the system must include a high voltage biasing circuit that is expensive and unreliable. Also, applying a large biasing voltage to the probe throughout the transmit cycle can shorten the life of the probe and introduce other circuit complexities.

Additional limitations and disadvantages of conventional and traditional approaches will become apparent to one of skill in the art, through comparison of such systems with some aspects of the present disclosure, as set forth in the remainder of the present application with reference to the drawings.

BRIEF DESCRIPTION

In accordance with embodiments herein, an ultrasound system is provided. The ultrasound system includes a transducer with piezoelectric transducer elements polarized in a poling direction. A transmit circuit is configured to generate a transmit signal having first and second polarity segments. The first and second polarity segments have corresponding first and second peak amplitude segments. A bias generator is configured to generate a bias signal in a direction of the poling direction. The bias signal is combined with the transmit signal to form a biased transmit signal that is shifted in the direction of the poling direction and still includes both of positive and negative voltages over a transmit cycle.

Optionally, the piezoelectric transducer elements may be formed from a single crystal material polarized in the poling direction. The single crystal material may represent a binary single crystal material. The bias signal may be a DC voltage that is applied continuously to the probe connector. The bias generator may be configured to generate the bias signal to have a steady-state voltage of between 2.5V and 10V. The bias generator may be configured to generate the bias signal to have a steady-state voltage of 4V to 6V. The bias generator may be configured to generate the bias signal to have a steady-state voltage of up to 15% of at least one of the first or second peak amplitudes of the transmit signal.

Optionally, the transmit signal may include a series of pulses that repeat. The pulses may have a predetermined pulse width to provide an active transmit signal for up to 5% of the transmit cycle. The bias generator may be configured to continuously apply the bias signal during 90% or more of the transmit cycle. The transmit signal may include a series of pulses that repeat, the pulses having a predetermined pulse width to provide an active transmit signal for up to 5% of the transmit cycle, the bias generator configured to continuously apply the bias signal during the transmit cycle.

Optionally, the ultrasound system may include a probe coupled to a distal end of a probe cable. The probe cable may include a probe connector at a proximal end of the probe cable. The probe connector may be configured to be connected to an ultrasound console. The bias generator may be located within the ultrasound console downstream of the transmit circuit and before the probe connector. The ultrasound system may comprise a probe. The bias generator may be located in the probe.

In accordance with embodiments herein, an ultrasound probe is provided. The ultrasound probe includes a transducer with piezoelectric transducer elements polarized in a poling direction. A probe connector and a transmit line extend from the probe connector to the transducer. The transmit line is configured to convey a transmit signal with different pattern. The different pattern segments have corresponding peak amplitudes. A bias generator is coupled to the transmit line. The bias generator is configured to generate a bias signal in a direction of the poling direction. The bias signal is combined with the transmit signal to form a biased transmit signal that is shifted in the direction of the poling direction and still includes both of positive and negative voltages over a transmit cycle. The bias signal may also be active during the receive time.

Optionally, the piezoelectric transducer elements may be formed from a single crystal material polarized in the poling direction. The single crystal material may represent a binary single or ternary crystal material. The bias generator may be configured to generate the bias signal to have a steady-state voltage of between 2.5V and 10V.

In accordance with embodiments herein, a method is provided. The method utilizes a transducer to transmit ultrasound signals and receive echo ultrasound signals from a region of interest. The transducer includes piezoelectric transducer elements polarized in a poling direction. The method generates a transmit signal having several polarity segments. The different polarity segments having corresponding different peak amplitudes. The method generates a bias signal in a direction of the poling direction and combines the bias signal with the transmit signal to form a biased transmit signal that is shifted in the direction of the poling direction and still includes both of positive and negative voltages over a transmit cycle. The bias signal may also be active during the receive time.

Optionally, the method may comprise providing the piezoelectric transducer elements formed from a single crystal material polarized in the poling direction. The method may utilize a binary or ternary single crystal material to form the transducer elements. The method may continuously apply a DC voltage as the bias signal. The method may comprise at least one of: generating the bias signal to have a steady-state voltage of up to 10V; generating the bias signal to have a steady-state voltage of up to 6V; generating the bias signal to have a steady-state voltage of up to 15% of at least one of the first or second peak amplitudes of the transmit signal; or continuously applying the bias signal during 90% or more of the transmit cycle.

In accordance with embodiments herein, an ultrasound system is provided that comprises: a transducer with piezoelectric transducer elements polarized in a poling direction, wherein over time one or more of the transducer elements possibility exhibit a depoling effect; and one or more drive circuits configured to: i) generate a transmit signal having at least first polarity segments, the first segments having corresponding first peak amplitudes; ii) generate a repoling signal having a repoling pattern configured to at least partially revert the depoling effect exhibited by the one or more transducer elements; and iii) generate a bias signal in the poling direction, the bias signal combined with the at least one of the transmit signal or the repoling signal to form a corresponding at least one of a biased transmit signal or a bias repoling signal, that is shifted in the poling direction.

Additionally or alternatively, the one or more drive circuits is further configured to generate the bias signal contemporaneous in time with the transmit signal, the bias signal combined with the transmit signal to form the biased transmit signal that is shifted in the poling direction. Additionally or alternatively, one or more drive circuits is further configured to generate the bias signal contemporaneous in time with the repoling signal, the bias signal combined with the repoling signal to form the biased repoling signal that is shifted in the poling direction. Additionally or alternatively, the one or more drive circuits include a transmit drive circuit configured to generate the transmit signal. Additionally or alternatively, the one or more drive circuits include a repoling drive circuit configured to generate the repoling signal. Additionally or alternatively, the one or more drive circuits include at least one common drive circuit configured to generate at least two of the transmit signal, the bias signal and the repoling signal. Additionally or alternatively, the one or more drive circuits are configured to generate, as the repoling signal, a series of at least one positive pulse and/or at least one negative pulse. Additionally or alternatively, the one or more drive circuits is configured to generate the repoling signal to have a voltage amplitude of up to 4 times greater than a voltage amplitude of the transmit signal.

In accordance with embodiments herein, an ultrasound probe is provided that comprises: a transducer with piezoelectric transducer elements polarized in a poling direction, wherein over time one or more of the transducer elements exhibit a depoling effect; a probe connector and a transmit line extending from the probe connector to the transducer, the transmit line configured to convey a transmit signal having at least first polarity segments, the first polarity segments having corresponding first peak amplitudes; the transmit line further configured to convey a repoling signal having a repoling pattern configured to at least partially revert the depoling effect exhibited by the one or more transducer elements; and a bias generator configured to generate a bias signal in a direction of the poling direction, the bias signal combined with the transmit signal to form a biased transmit signal that is shifted in the direction of the poling direction and still includes both of positive and negative voltages over a transmit cycle.

Additionally or alternatively, the bias generator is further configured to generate the bias signal contemporaneous in time with the repoling signal, the bias signal combined with the repoling signal to form a biased repoling signal that is shifted in the poling direction. Additionally or alternatively, a repoling drive circuit is provided within a housing of the ultrasound probe, the repoling drive circuit configured to generate the repoling signal. Additionally or alternatively, the repoling signal includes a series of at least one positive pulse and at least one negative pulse. Additionally or alternatively, the repoling signal has a voltage amplitude of up to 4 times greater than a voltage amplitude of the transmit signal.

In accordance with embodiments herein, a method is provided that comprises: utilizing a transducer to transmit ultrasound signals and receive echo ultrasound signals from a region of interest, the transducer including piezoelectric transducer elements polarized in a poling direction, wherein over time one or more of the transducer elements exhibit a depoling effect; generating a transmit signal having at least first polarity segments, the first polarity segments having corresponding first peak amplitudes; generating a repoling signal having a repoling pattern configured to at least partially revert the depoling effect exhibited by the one or more transducer elements; and generating a bias signal in the poling direction, the bias signal combined with the at least one of the transmit signal or the repoling signal to form a corresponding at least one of a biased transmit signal or a bias repoling signal, that is shifted in the poling direction.

Additionally or alternatively, the generating the bias signal includes generating the bias signal contemporaneous in time with the transmit signal, the bias signal combined with the transmit signal to form the biased transmit signal that is shifted in the poling direction. Additionally or alternatively, the generating the bias signal further comprises generating the bias signal contemporaneous in time with the repoling signal, and combining the bias signal with the repoling signal to form the biased repoling signal that is shifted in the poling direction. Additionally or alternatively, the repoling signal is generated after at least one of completion of acquisition of ultrasound data for an ultrasound image frame or during a freeze mode. Additionally or alternatively, the repoling signal comprises a series of at least one positive pulse and at least one negative pulse. Additionally or alternatively, the repoling signal has a voltage amplitude of up to 4 times greater than a voltage amplitude of the transmit signal. Additionally or alternatively, the method continuously applies a DC voltage as the bias signal to both the transmit signal and the repoling signal.

DETAILED DESCRIPTION

Figure 1:
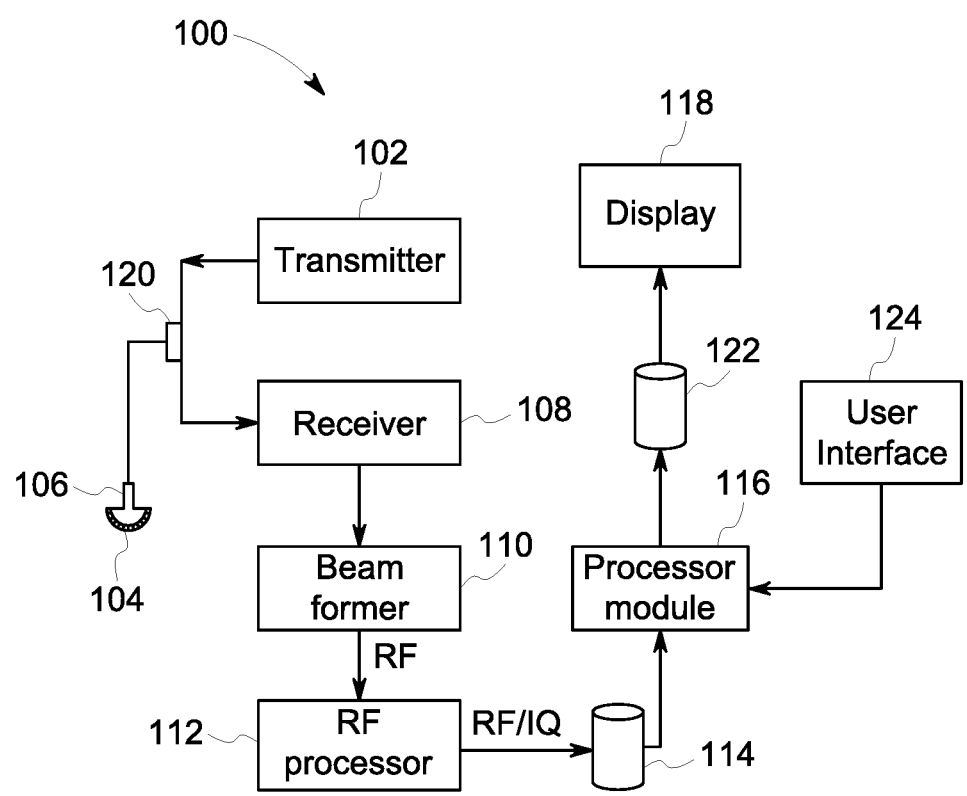
FIG. 1 illustrates an ultrasound system including a transmitter that drives an array of transducer elements within a probe to emit pulsed ultrasonic signals into a body in accordance with embodiments herein.

The foregoing summary, as well as the following detailed description of certain embodiments will be better understood when read in conjunction with the appended drawings. To the extent that the Figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general-purpose signal processor or a block of random-access memory, hard disk, or the like) or multiple pieces of hardware. Similarly, the programs may be stand-alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized, and that structural, logical and electrical changes may be made without departing from the scope of the various embodiments. The following detailed description is, therefore, not to be taken in a limiting sense, and the scope of the present invention is defined by the appended claims and their equivalents.

As used herein, an element or step recited in the singular and proceeded with the word "a" or "an" should be understood as not excluding plural of said elements or steps, unless such exclusion is explicitly stated. Furthermore, references to "an embodiment," "one embodiment," "a representative embodiment," "an example embodiment," "various embodiments," "certain embodiments," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

The term "sensitivity" shall mean the ratio of electrical output to signal input or signal output to electrical input.

The term "depoling effect" shall mean a change between i) a present level or degree to which a transducer element is polarized and ii) a prior level or degree to which the transducer element was polarized. The prior level or degree of polarization may be defined as a baseline polarization level. As an example, a depoling effect may represent a reduction in the level or degree of polarization relative to a level of polarization exhibited at a time of manufacture, assembly or refurbishment of an ultrasound probe or transducer. For the avoidance of doubt, it is recognized that a transducer element may exhibit various levels of the depoling effect (e.g., small, medium or large amounts of depoling). Also, for the avoidance of doubt, it is recognized that a new or initial transducer element (e.g., recently manufactured, recently refurbished, unused) may not be completely polarized. Instead, the degree to which the transducer elements are initially polarized may be used as a reference or base polarization level/degree.

Embodiments herein may be implemented in connection with the structure and functions described in one or more of the following published patent applications: U.S. Pat. No. 9,966,578, issued May 8, 2018, entitled "SEAL RING AND ASSOCIATED METHOD"; U.S. Pat. No. 8,978,216, issued Mar. 17, 2015, entitled "METHOD FOR FORMING AN ACOUSTICAL STACK FOR AN ULTRASOUND PROBE"; U.S. Pat. No. 7,621,028, issued Nov. 24, 2009, entitled "METHOD FOR OPTIMIZED DEMATCHING LAYER ASSEMBLY IN AN ULTRASOUND TRANSDUCER"; U.S. Pat. No. 7,545,012, issued Jun. 9, 2009, entitled "CAPACITIVE MICROMACHINED ULTRASOUND TRANSDUCER FABRICATED WITH EPITAXIAL SILICON MEMBRANE"; U.S. Pat. No. 7,289,336, issued Oct. 30, 2007, entitled "ELECTRONIC PACKAGING AND METHOD OF MAKING THE SAME"; U.S. Pat. No. 7,094,444, issued Aug. 22, 2006, entitled "METHOD FOR PREPARING COATED COMPONENTS USING NIAL BOND COATS"; U.S. Pat. No. 7,078,073, issued Jul. 18, 2006, entitled "METHOD FOR REPAIRING COATED COMPONENTS"; U.S. Pat. No. 6,6666,825, issued Dec. 23, 2003, entitled "ULTRASOUND TRANSDUCER FOR IMPROVING RESOLUTION IN IMAGING SYSTEM". The complete subject matter of the published patents, patent applications and other publications referenced above, and hereafter, are expressly incorporated herein by reference in their entirety.

Embodiments herein may be implemented in connection with a variety of ultrasound transducers without limitation on a geometry of the transducer. However, implementations herein may have better suitability in connection with transducers that are made from materials susceptible to depoling, including (but not limited to) single crystal materials and the like. In particular, embodiments herein are well-suited to limit or eliminate the depoling effect in transducer elements that are constructed substantially from binary or ternary single crystal materials or having a substantially homogeneous composition of binary or ternary single crystal materials. In particular, embodiments herein utilize low voltage bias signals to stabilize weaker binary single crystal materials when utilizing bias signals having lower voltage, as compared to the voltage levels of bias signals used with ternary single crystal materials.

Embodiments may be implemented in connection with ultrasound probes having various types and arrangements of transducers that are configured to collect any and all types of ultrasound data sets, including (but not limited to) B-mode data, power Doppler data, Doppler data, strain data, two-dimensional data, three-dimensional data, four dimensional data, shear wave data or otherwise, as described herein and as described in the patents, patent applications and other publications referenced and incorporated herein.

While the primary embodiments are described in connection with ultrasound transducers utilized in connection with diagnostic imaging, it is recognized that embodiments may be implemented in connection with ultrasound transducers utilized for other applications. Nonlimiting examples of other applications for ultrasound transducers include ultrasound therapy systems (e.g., ultrasound based treatment of tumors, ultrasound based removal of fat tissue), opto-acoustic ultrasound, sonar, ultrasound based inspection of mechanical structures, ultrasound based inspection of mechanical connections (e.g., welds and other bonded interfaces) and the like. Traditionally, transducers for therapy, sonar and inspection applications have utilized different crystal structures that were less susceptible to depoling (e.g., not single crystal materials), and thus were not able to take advantage of other benefits offered by single crystal structures. For example, the higher voltages utilized in connection with therapy, sonar and inspection applications may otherwise accelerate the depoling process and the degradation of the transducer, thereby rendering single crystal structures unsuited for such applications. However, with the addition of the improvements described herein, depoling is avoided, even at higher transmit voltages, thereby allowing single crystal transducers to be used in higher voltage applications.

FIG. 1 illustrates an ultrasound system 100 including a transmitter 102 that drives an array of transducer elements 104 (e.g., piezoelectric elements) within a probe 106 to emit pulsed ultrasonic signals into a body. The elements 104 may comprise a single crystal material as discussed herein. The elements 104 may be arranged, for example, in one or two dimensions. A variety of geometries may be used, and the probe 106 may be capable of acquiring one, two, three and/or four-dimensional image data. The system 100 may have a probe port 120 for connecting the probe 106 or the probe 106 may be hardwired to the system 100.

The transmitter and the ultrasound probe may be implemented and/or configured for one-dimensional (1D), two-dimensional (2D), three-dimensional (3D), and/or four-dimensional (4D) ultrasound scanning. The ultrasound probe may comprise a one-dimensional (1D, 1.25D, 1.5D or 1.75D) array or a two-dimensional (2D) array of piezoelectric elements. The ultrasound probe may comprise a group of transmit transducer elements and a group of receive transducer elements, that normally constitute the same elements. The transmitter may be driven by the transmit beamformer. The transmit beamformer may comprise suitable circuitry that may be operable to control the transmitter which, through a transmit sub-aperture beamformer, drives the group of transmit transducer elements to emit ultrasonic transmit signals into a region of interest (e.g., human, animal, underground cavity, physical structure and the like). In this regard, the group of transmit transducer elements can be activated to transmit ultrasonic signals. The ultrasonic signals may comprise, for example, pulse sequences that are fired repeatedly at a pulse repetition frequency (PRF), which may typically be in the kilohertz range. The pulse sequences may be focused at the same transmit focal position with the same transmit characteristics. A series of transmit firings focused at the same transmit focal position may be referred to as a "packet."

The ultrasonic signals are back scattered from structures in the body, like fatty tissue or muscular tissue, to produce echoes that return to the elements 104. The echoes are received by a receiver 108. The received echoes are passed through a beamformer 110 that performs beamforming and outputs a radiofrequency (RF) signal. The RF signal then passes through an RF processor 112. Alternatively, the RF processor 112 may include a complex demodulator (not shown) that demodulates the RF signal to form in-phase and quadrature (IQ) data pairs representative of the echo signals. The RF or IQ signal data may then be routed directly to a memory 114 for storage.

The ultrasound system 100 also includes a processor module 116 to process the acquired ultrasound information (e.g., RF signal data or IQ data pairs) and prepare frames of ultrasound information for display on display 118. The processor module 116 is adapted to perform one or more processing operations according to a plurality of selectable ultrasound modalities on the acquired ultrasound information. Acquired ultrasound information may be processed and displayed in real-time during a scanning session as the echo signals are received. Additionally or alternatively, the ultrasound information may be stored temporarily in memory 114 or memory 122 during a scanning session and then processed and displayed in an off-line operation.

A user interface 124 may be used to input data to the system 100, adjust settings, and control the operation of the processor module 116. The user interface 124 may have a keyboard, trackball and/or mouse, and a number of knobs, switches or other input devices such as a touchscreen. The display 118 includes one or more monitors that present patient information, including diagnostic ultrasound images to the user for diagnosis and analysis. One or both of memory 114 and memory 122 may store two-dimensional (2D) and/or three-dimensional (3D) datasets of the ultrasound data, where such datasets are accessed to present 2D and/or 3D images. Multiple consecutive 3D datasets may also be acquired and stored over time, such as to provide real-time 3D or four-dimensional (4D) display. The images may be modified and the display settings of the display 118 also manually adjusted using the user interface 124.

Figure 2:
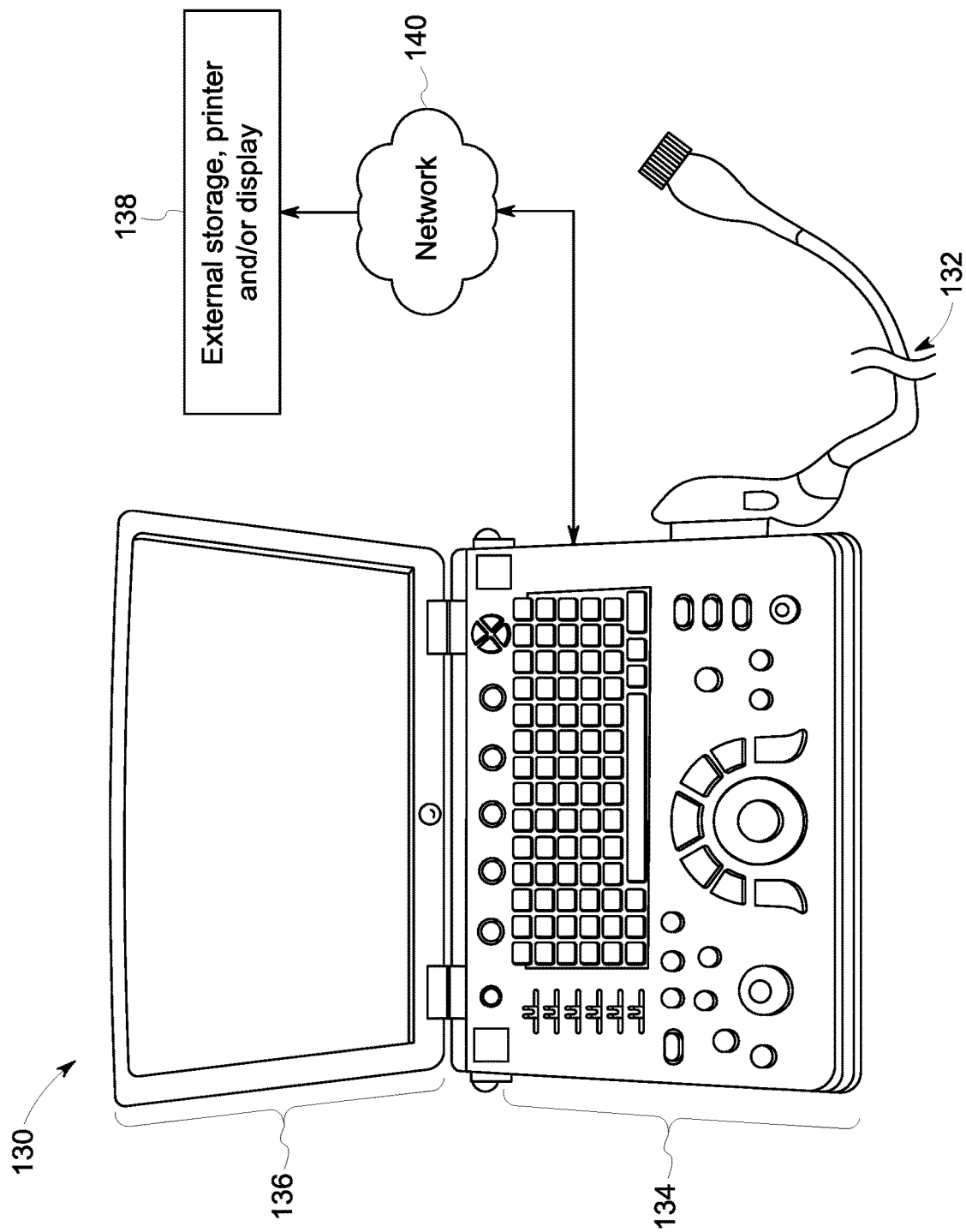
FIG. 2 illustrates a 3D-capable miniaturized ultrasound system having a probe that may comprise elements having single crystal material and/or single crystal composite material in accordance with embodiments herein.

FIG. 2 illustrates a 3D-capable miniaturized ultrasound system 130 having a probe 132 that may comprise elements 104 having single crystal material as discussed herein. The probe 132 may be configured to acquire 3D ultrasonic data. For example, the probe 132 may have a 2D array of transducer elements 104. A user interface 134 (that may also include an integrated display 136) is provided to receive commands from an operator.

As used herein, "miniaturized" means that the ultrasound system 130 is a handheld or hand-carried device or is configured to be carried in a person's hand, pocket, briefcase-sized case, or backpack. For example, the ultrasound system 130 may be a hand-carried device having a size of a typical laptop computer, for instance, having dimensions of approximately 2.5 inches in depth, approximately 14 inches in width, and approximately 12 inches in height. The ultrasound system 130 may weigh about ten pounds, and thus is easily portable by the operator. The integrated display 136 (e.g., an internal display) is also provided and is configured to display a medical image.

The ultrasonic data may be sent to an external device 138 via a wired or wireless network 140 (or direct connection, for example, via a serial or parallel cable or USB port). In some embodiments, external device 138 may be a computer or a workstation having a display. Alternatively, external device 138 may be a separate external display or a printer capable of receiving image data from the hand carried ultrasound system 130 and of displaying or printing images that may have greater resolution than the integrated display 136. It should be noted that the various embodiments may be implemented in connection with a miniaturized ultrasound system having different dimensions, weights, and power consumption.

Figure 3:
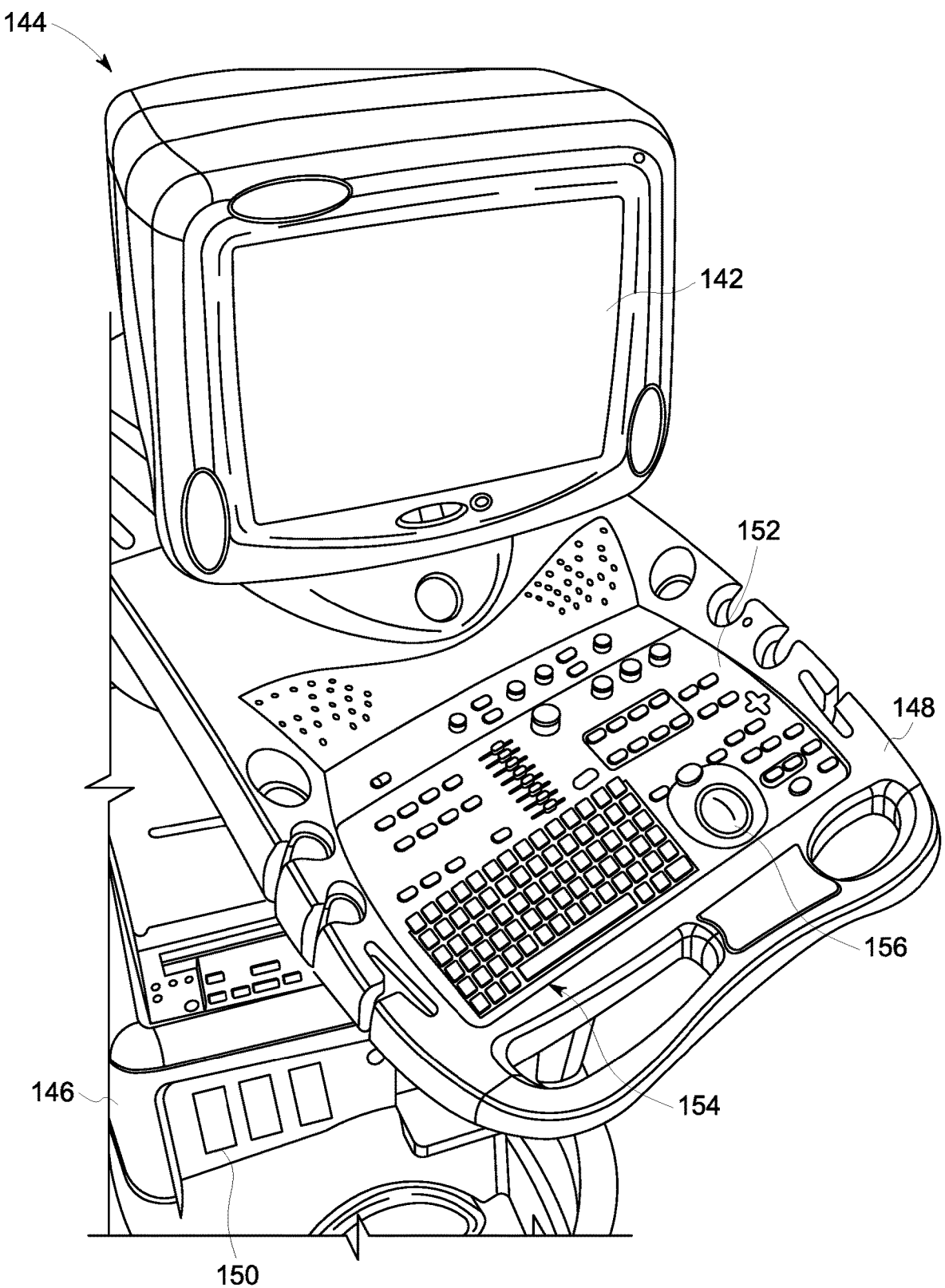
FIG. 3 illustrates a mobile ultrasound imaging system provided on a movable base in accordance with embodiments herein.

FIG. 3 illustrates a mobile ultrasound imaging system 144 provided on a movable base 146. The ultrasound imaging system 144 may also be referred to as a cart-based system. A display 142 and user interface 148 are provided and it should be understood that the display 142 may be separate or separable from the user interface 148. The system 144 has at least one probe port 150 for accepting probes (not shown) that may have elements 104 that comprise single crystal material as discussed herein.

The user interface 148 may optionally be a touchscreen, allowing the operator to select options by touching displayed graphics, icons, and the like. The user interface 148 also includes control buttons 152 that may be used to control the system 144 as desired or needed, and/or as typically provided. The user interface 148 provides multiple interface options that the user may physically manipulate to interact with ultrasound data and other data that may be displayed, as well as to input information and set and change scanning parameters. The interface options may be used for specific inputs, programmable inputs, contextual inputs, and the like. For example, a keyboard 154 and track ball 156 may be provided.

Figure 4:
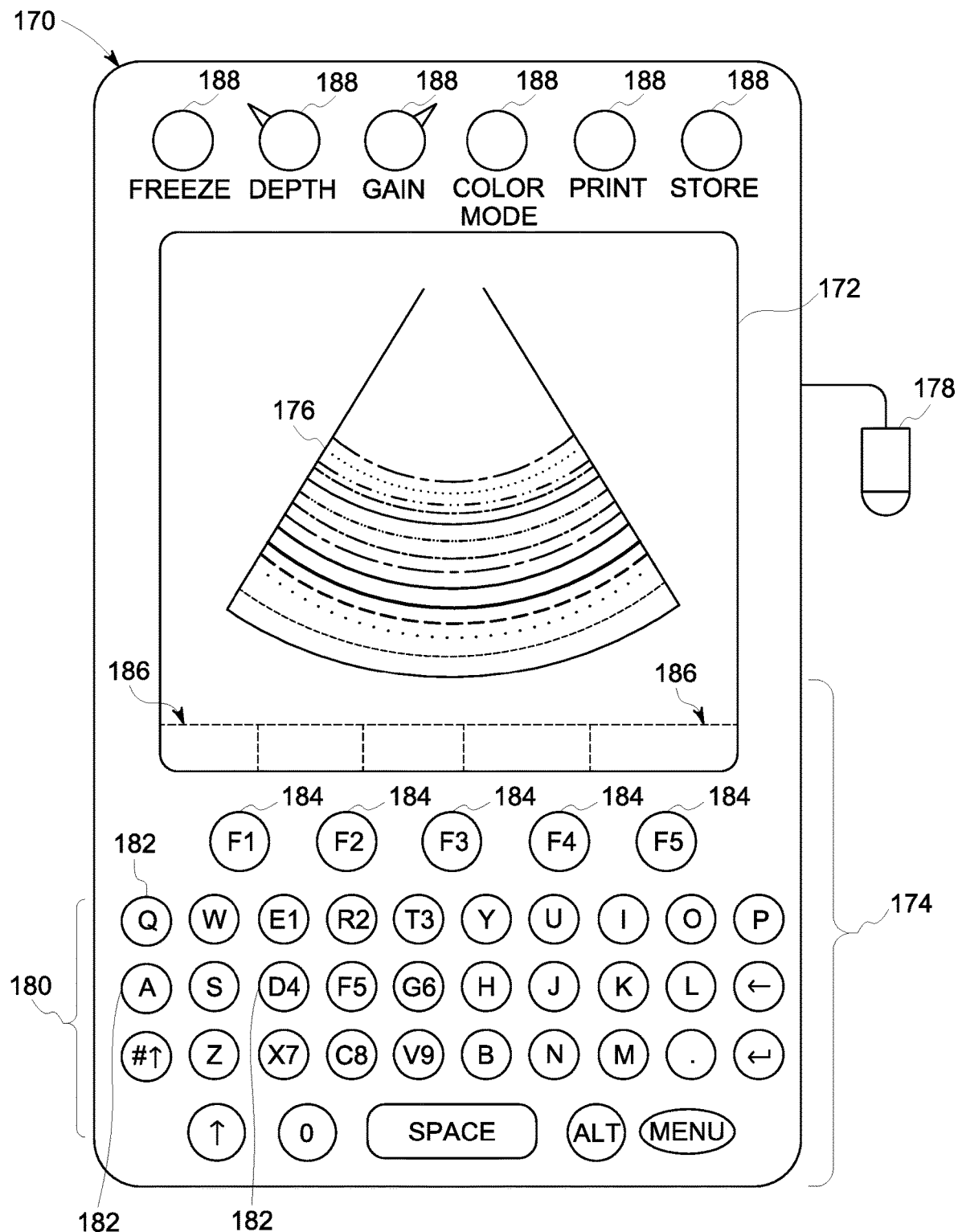
FIG. 4 illustrates a hand carried or pocket-sized ultrasound imaging system wherein display, and user interface form a single unit in accordance with embodiments herein.

FIG. 4 illustrates a hand carried or pocket-sized ultrasound imaging system 170 wherein display 172 and user interface 174 form a single unit. By way of example, the pocket-sized ultrasound imaging system 170 may be approximately 2 inches wide, approximately 4 inches in length, and approximately 0.5 inches in depth and weighs less than 3 ounces. The display 172 may be, for example, a 320×320 pixel color LCD display (on which a medical image 176 may be displayed). A typewriter-like keyboard 180 of buttons 182 may optionally be included in the user interface 174. The system 170 is connected to a probe 178 that has transducer elements 104 comprising a single crystal material as discussed herein. Multi-function controls 184 may each be assigned functions in accordance with the mode of system operation. Therefore, each of the multi-function controls 184 may be configured to provide a plurality of different actions. Label display areas 186 associated with the multi-function controls 184 may be included as necessary on the display 172. The system 170 may also have additional keys and/or controls 188 for special purpose functions, which may include, but are not limited to "freeze," "depth control," "gain control," "color-mode," "print," and "store."

The term acoustical stack may be used herein to refer to several layers that are attached together in a stacked configuration. Each of the elements 104 (shown in FIG. 1)

within the probe 106 comprises an acoustical stack. In one embodiment, the acoustical stack includes a piezoelectric layer that is formed of a piezoelectric material such as single crystal piezoelectric material. The piezoelectric layer may have, for example, a thickness of approximately ½ or ¼ of λ, wherein λ is the wavelength of sound in the piezoelectric material for the desired center frequency of the useful bandwidth. Electrodes may be formed with a thin metallic layer and deposited on at least top and bottom sides of the piezoelectric material.

Figure 5:
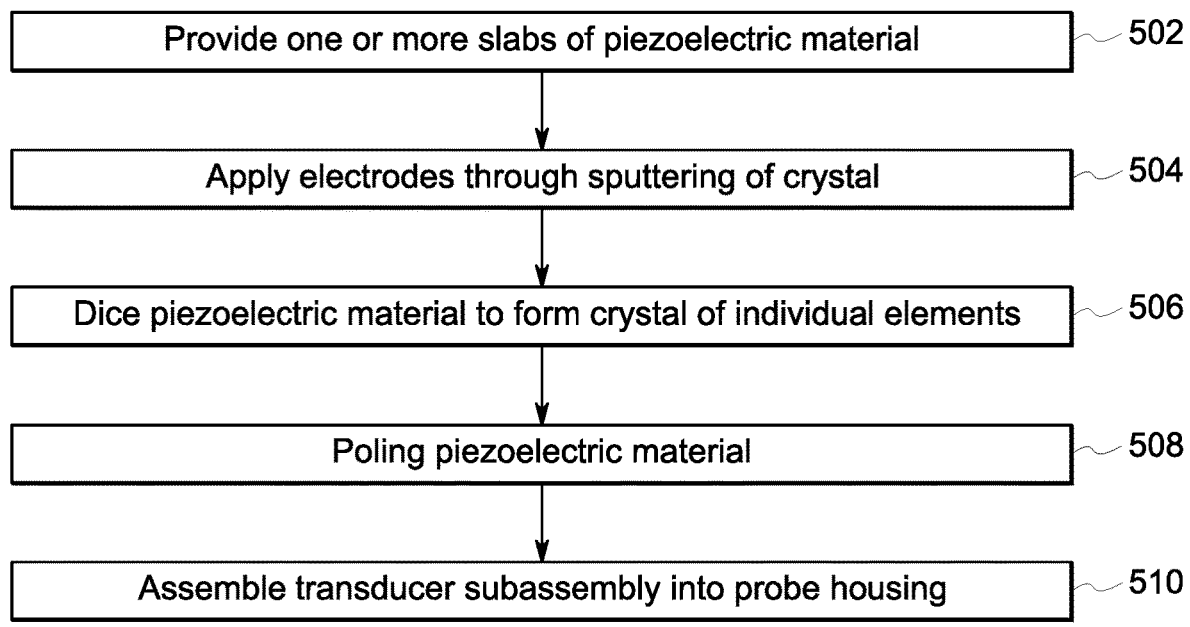
FIG. 5 illustrates a method for manufacturing a transducer array in accordance with embodiments herein.

FIG. 5 illustrates a method for manufacturing a transducer array in accordance with embodiments herein. At 502, a slab of a piezoelectric material is provided. The slab of piezoelectric material may also be referred to as a piezoelectric substrate, which may be formed form different types of piezoelectric compounds. Typically, the piezo-material is fully metallized on the outside surface. The metallization forms the individual element electrodes after dicing the acoustic stack into individual elements. In accordance with at least some embodiments, the substrate may be formed as a single crystal material. While the single crystal material may be a binary or ternary single crystal material, more preferably, the single crystal material is a binary single crystal material. Non-limiting examples of single crystal materials that may be utilized include bi-composites such as lead zirconium niobate-lead titanate (PZN-PT) and lead magnesium niobate-lead titanate (PMN-PT). PMN-PT has an internal structure that induce different but specific characteristics. PMN-PT exhibits piezoelectric properties and is composed of two different groups of atoms that behave as a unit, each an oxide, called radicals (e.g., Pb(Mg1/3 Nb2/3) O3 and PbTiO3). PMN-PT is part of the relaxor-ferroelectric material class, and has a monocrystalline structure, unlike commonly used piezoelectric materials that have a granular piezoceramic structure. This means that defects and grain boundaries are absent and thus PMN-PT can be machined to a more precise degree, with optical grade finish. Other properties that differentiate PMN-PT from granular piezoelectric materials, such as PZT, are also directly linked to the monocrystalline structure. Such properties are optical, mechanical or electrical and can be anisotropic (directly dependent). Another advantage of PMN-PT having a monocrystalline structure is its uniformity, ensuring consistent values for the piezoelectric coefficients.

The piezoelectric substrate includes a proximal or front surface and a distal or back surface. Once the substrate is assembled into an ultrasound probe, during operation of the probe, the probe is positioned against a region of interest and ultrasound waves are transmitted in a scanning direction into the ROI. Structures within the ROI signals in response to the transmitted ultrasound waves. In medical imaging and therapy applications, the probe is held against tissue for an ROI, with the front face of the probe generally oriented perpendicular to the scanning direction. In non-destructive testing, the probe is held against a structure that includes an ROI with the scanning direction extending into the ROI. In sonar applications, the probe is located within a fluid (e.g., ocean). The proximal surface is the surface of the substrate located closest to (or against) the tissue, structure or fluid containing the ROI with the scanning direction extending into the ROI.

In accordance with some probe designs, the proximal and distal surfaces of the substrate may extend along generally parallel planes (e.g., for linear transducer configurations). Optionally, the proximal and distal surfaces may extend along generally concentric arcs (e.g., for curved transducer configurations). Optionally, the proximal and/or distal surfaces may be constructed to extend along other paths that are not planar and/or do not have a constant curve. For example, at least the proximal surface may extend in a planar manner in a first direction (e.g., longitudinal direction), but extend along a curved path in an orthogonal second direction (e.g., transverse direction). The proximal and distal surfaces of the substrate are spaced apart from one another by a depth or thickness of the substrate as measured along a depth direction. In generally, the proximal and distal surfaces of the substrate may be oriented generally parallel to one another, although in certain embodiments, the proximal and distal surfaces may be oriented at a non-parallel angle to one another.

At 504, the piezoelectric substrate is "poled" by applying an electric field to the piezoelectric substrate along a predetermined direction. Prior to the poling operation, the piezoelectric substrate exhibits a non-polarized state formed from electric dipoles that are at least partially randomly oriented. When in the non-polarized state, the substrate exhibits a relatively weaker piezoelectric sensitivity as compared to after poling. The poling operation orients the electrical dipoles within the substrate in a common direction referred to as a "poling direction". The polarization of the piezo material is in a transmit direction, that is in the vertical direction of the acoustic stack. The vertical direction extends in a radial direction for a curved probe, and in a longitudinal direction for a linear or phased probe.

By way of example, one or an array of proximal electrodes may be connected at or near the proximal surface of the substrate with the electrodes arranged in a pattern corresponding to a pattern of transducer elements to be utilized by the probe. The distal surface of the substrate may be connected to a similar array of distal electrodes, fewer electrodes and/or a common electrode. A voltage potential is applied across the proximal and distal electrodes to form the electric field. The electric field is applied with sufficient strength to reorient the electrical dipoles within the piezoelectric substrate to be aligned along a common direction, namely aligned along the scanning direction. For linear probes, the scanning direction extends generally parallel to the depth axis and perpendicular to the face of the probe. For curved probes, in connection with a single transmit operation, the scanning direction extends parallel to a local depth axis (proximate to a transmit axis) and perpendicular to a local region of the probe proximate to the transmit axis.

The poling direction (and orientation of the dipoles) generally extends in a direction between the electrodes coupled to the transducer elements. The electrodes may be positioned on front/proximal and rear/distal surfaces of the transducer elements (or stack). Therefore, the poling direction extends parallel to the depth axis of the stack of the transducer elements. As another example, the transducer elements are arranged in an array in the probe where the probe has a front/proximal surface configured to be positioned proximate to a region of interest. The front surface of the probe extends along a plane. The poling direction generally extends perpendicular to the plane of the front surface of the probe and array of transducer elements.

At 506, the substrate of piezoelectric material is diced using dicing parameters or conditions. For example, the dicing operation may fully dice through all acoustic layers, such as to dice through all electrically conductive layers to separate all acoustic elements and allow for individual electrical connections. Additionally, elements may be sub-diced to achieve special aspect ratios and preferable vibration modes. Sub-dicing, however, still maintains electric connection for element sub-parts. Optionally, the dicing operation may be limited to partly or partially dicing the substrate material(s) partway through, such that the substrate material is maintained as a slab rather than individual pieces. Optionally, the dicing parameters or conditions may be based on the mechanical properties and geometry of single crystal. Dicing parameters may include, but are not limited to, blade material, spindle speed of rotation, feeding speed and the like. Therefore, the quality of the single crystal is maintained while avoiding the cracking and degrading experienced when using dicing conditions that are needed when dicing an entire acoustical stack. The process for manufacturing the acoustic stack introduces stresses, both in ceramics and single crystal materials. Typically, an annealing step is performed to stress relieve the materials before poling the elements.

In another embodiment, laser cutting, ion milling, chemical etching, wire dicing, plasma, and/or other processes or methods may be used and may be optimized based on the single crystal material. In one embodiment the slab of single crystal material may be a single piece of material, and in another embodiment the slab of single crystal material may be a stack of two or more slabs of single crystal material. Generally, the dicing operation cuts fully through the layers to separate the electrical connections. The dicing operation creates single crystal pieces, each of which corresponds to a single element in the probe. A kerf may extend from the proximal or front surface of the slab through the single crystal material. In one embodiment, the kerf may be a separation, that is, the kerf may completely separate the single crystal pieces. The kerf has a width corresponding to the width of the first dicing. The kerfs are filled with a kerf filling material. The kerf filling material may be a silicon material, organic polymer, epoxy based material, or other material that is suitable for both filling the kerf and suitable for the subsequent dicing operation that will dice the acoustical stack.

At 508, an electrode array is sputtered on the piezo material before the part is laminated into the stack. For example, at least the proximal and distal surfaces of the piezoelectric material may be coated with a layer of a conductive material such as gold, nickel, a combination of conductive materials, and the like. Isolation scribings may be made on the proximal and distal surfaces of the crystal to define signal areas and ground areas.

It should be understood that other methods may be used to form electrodes and/or define signal and ground areas. For example, high frequency arrays may be formed with elements that are defined by pre-shaped electrodes on piezo-materials. In the foregoing example, no dicing operation is performed. For example, dicing may be avoided in high frequency arrays where a dicing cut of, for example 30 um width, would take too much of the pitch in the material and is thus technically not feasible. Optionally, at least one matching layer may be fixed, such as by using an adhesive, glue or other material, to the side of the crystal that does not have the isolation scribings. A flex circuit is sandwiched or layered within the acoustical stack to interconnect the stack with the system 100. The flex circuit has a flex insulation layer that may be formed of a material such as Kapton, which is a polyimide film. Other materials may be used. Upper traces are formed on one side of the flex insulation layer and lower traces are formed on the other side of the flex insulation layer. In one embodiment the upper and lower traces may be copper or another metallic material or combination of materials, and may be printed on the flex insulation layer using printing methods known in the art.

At 510, the transducer subassembly is assembled into a probe housing, along with any other electrical or mechanical components appropriate to fully assemble an ultrasound probe. Next, the discussion turns to methods and systems to manage operation of an ultrasound probe to limit or eliminate depoling of the piezoelectric material in accordance with embodiments herein. During operation, a transmit voltage is applied to the probe, which leads to an electric field in the transducer. The electric field results in a mechanical dimension change of the transducer element based on the piezoelectric effect. The mechanical dimension change is used to create an acoustic wave which is emitted by the probe. The acoustic wave is partially reflected at different anatomical layers within a region of interest. The reflected waves impact the transducers and cause mechanical distortions of transducer elements. The mechanical distortions create an electric field across the corresponding transducer element, again based on the piezoelectric effect. The electric field within an individual transducer element creates an electrical potential between the electrodes connected to the corresponding transducer element. The electrical potential is sensed as raw receive ultrasound signals and processed to form ultrasound data and ultrasound images.

If unduly high voltages are applied to the transducer elements in a direction opposite to the poling direction, the high voltages degrade the piezoelectric effect exhibited by the transducer elements. For example, the high voltages reorient at least a portion of the electrical dipoles within the composition of the transducer elements, thereby reintroducing at least a partial non-polarization state to the composition of the transducer elements. The degradation in the polarization of the transducer elements reduces the piezoelectric effect exhibited by the transducer elements which leads to lowered sensitivity of the ultrasound probe. The amount of depoling, or degradation in the piezoelectric effect, for a particular probe will depend on various factors, such as voltage amplitude, transducer temperature and/or a signal pattern applied in connection with transmit signals. Complex voltage signal patterns applied during the transmit signals may become more relevant to potential depoling. For example, some voltage signal patterns may have segments with an increased amount of time and/or voltage level that is opposite to the poling direction. The potential for depoling increases as the number or length of segments increases that are opposite to the poling direction.

When simpler transmit signals are utilized, the amount of depoling and degradation may depend on an ending voltage polarity of each transmit signal (e.g., positive or negative voltage) with respect to the polarization direction. For example, an ending of voltage polarity that corresponds to the polarity of the poling direction would have little or no depoling affect, whereas an ending voltage polarity that is opposite to the polarity of the poling direction may have a limited depoling effect.

The negative effects associated with the depoling represent a substantial challenge in connection with newer types of probe designs, and in particular in connection with ultrasound probes utilizing single crystal materials for the transducer arrays. During extensive analysis inventors of the present application observed that depoling could be substantially eliminated in at least certain crystal materials when a "low" level DC bias voltage was applied to the transducer elements during at least transmit operations. The level of the DC bias voltage was defined in terms of a ratio or relation to the voltage applied during transmit operations. In accordance with at least certain embodiments, the low-level DC bias voltage was maintained at or below 15% of the peak voltage applied during a transmit operation. For example, when the transmit voltage is varied between +/−60 V, the DC bias voltage was maintained at or below +/−9 V. By maintaining the DC bias voltage as a small percentage of the transmit voltage, embodiments herein stabilize the electrical dipole orientation of the composition within the transducer elements and thus avoid (or at least substantially diminish) depoling effects.

Further, it was found that, if the DC bias voltage is present for a long period of time within a transmit and receive cycle compared to a length of the transmit voltage pulse, the low-level DC bias voltage stabilized the electrical dipole orientation of the composition within the transducer elements. For example, the DC bias voltage may be maintained continuously throughout an entire transmit and receive cycle and/or maintained for a substantial majority of the transmit and receive cycle (e.g., 90% or more). By way of example, the transmit signal may include a series of pulses that repeat, where the pulses have a predetermined pulse width to provide an active transmit signal for up to 5% of a complete transmit and receive cycle. As a further example, in connection with a B-mode imaging procedure, the imaging sequence (transmit and receive cycle) may include a series of transmit pulses that repeat every 200 μs, where each individual pulse width ranges between 200 and 500 ns, thereby providing an active transmit signal for approximately 5% of the time over the course of an entire transmit operation. The DC bias voltage may be continuously applied during the entire transmit cycle and/or maintained for 90% or more of the transmit cycle.

Optionally, the duty cycle for the DC bias voltage may be varied based on the type of imaging operation and the corresponding type of transmit signal. For example, during a pulse wave Doppler imaging mode, the transmit signal will exhibit a different shape, pulse width and duty cycle, as compared to the transmit signal associated with B-mode imaging. Similarly, the DC bias voltage applied during pulse wave Doppler imaging may be varied. By utilizing a DC bias voltage set to a low percentage of the maximum transmit voltage and by maintaining the DC bias voltage for a substantially longer period of time relative to the pulse width of transmit pulses, it was found that embodiments herein were able to disproportionately increases a maximum transmit voltage for different transducer materials. The disproportionate increase in maximum transmit voltage was able to be sustained without experiencing depoling effect degradation or a decrease in sensitivity. The disproportionate increase in maximum transmit voltage is relative to conventional approaches that utilize no DC bias voltage and relative to conventional approaches that utilize a significantly high DC bias voltage substantially corresponding to the maximum transmit voltage (e.g., such as described by Dillman et al.). Therefore, in accordance with embodiments herein, a voltage of only a few volts can lead to a significant increase of the possible transmit voltage (several tens of volts). At least one benefit of the embodiments herein is, that low voltages lead to a significant improvement if the voltage is applied for a long time compared to transmit voltage signal length and at the same time provide a much simpler and cost-effective solution by utilizing a low voltage DC bias circuit.

By substantially eliminating the effects of depoling, embodiments herein provide probes that are capable of operating transducers with higher voltages, as compared to conventional probes, which thereby increases image quality. Additionally, by substantially eliminating the effects of depoling, embodiments herein provide probes that are capable of using transmit patterns which provide better image quality, where such transmit patterns could not be used in the past because of depoling effects. Further, embodiments herein may be implemented as retrofit solutions to be backward compatible with existing probes, such as through a design change that is applied at a console of the ultrasound imaging system. By applying a retrofit solution, embodiments improve performance of existing products in the installed base.

Figure 6A:
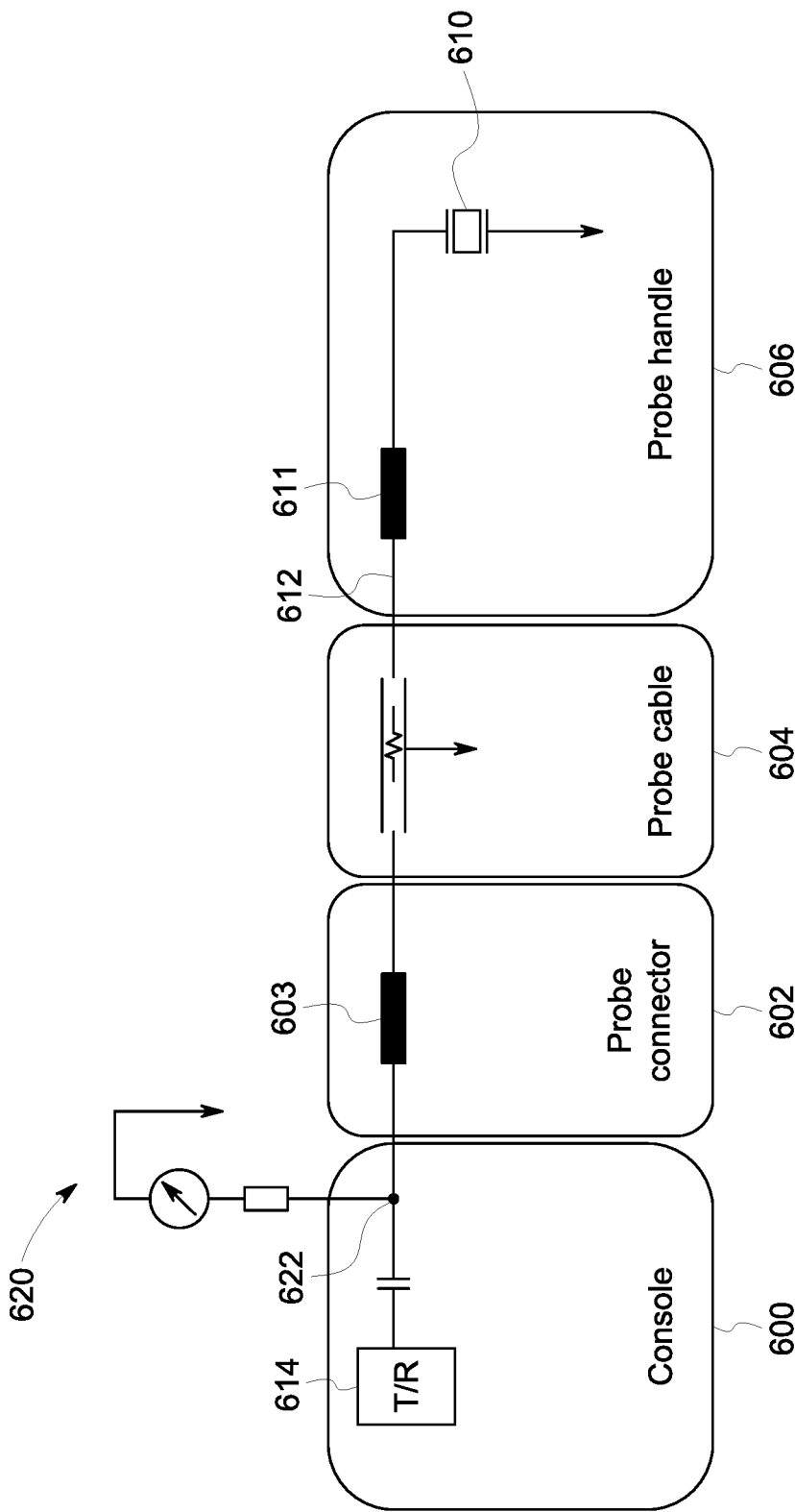
FIG. 6A illustrates a block diagram of an ultrasound system including a DC bias circuit implemented in accordance with embodiments herein.

FIG. 6A illustrates a block diagram of an ultrasound system including a DC bias circuit implemented in accordance with embodiments herein. The ultrasound system includes a console 600 that is connected to a probe connector 602. The console 600 may include all or a portion of the components described and illustrated in connection with one or more of FIGS. 1-4. The probe connector 602 is provided on a proximal end of a probe cable 604. A distal end of the probe cable 604 is connected to a probe 606. A transmit line 612 electrically connects a transducer element 610 to corresponding contacts (not shown) in the probe connector 602. The probe connector 602 is configured to be mated with a mating connector provided on the console (not shown). An inductor 611, within the probe 606, and an inductor 603, within the probe connector 602, are provided along line 612. The probe cable 604 is connected at the probe connector 602 to a transmit/receive (T/R) circuit 614 within the console 600. In the example of FIG. 6A, the transmit line 612 may also be utilized as a receiver line to convey receive signals from the transducer element to the transceiver 614. Optionally, separate transmit and receive lines may be utilized. A capacitor is provided between the T/R circuit 614 and the node 622.

During transmit operations, the T/R circuit 614 delivers a transmit signal to cause the transducer element 610 to transmit ultrasound signals. During receive operations, the T/R circuit 614 records return "echo" signals along line 612 corresponding to ultrasound echo waves sensed at the transducer element 610. A biasing circuit 620 is connected at node 622 within the console 600. The biasing circuit 620 is configured to introduce a bias signal, such as a DC bias voltage, onto the line 612. The bias signal is superimposed at node 622 onto the transmit signal generated by the transmit/receive circuit 614.

FIG. 6A illustrates a simplified diagram associated with a single transducer element 610, although it is understood that the probe 606 will include a transducer array with multiple transducer elements, multiple lines and T/R circuits associated therewith. In accordance with embodiments herein, a common biasing circuit 620 may generate and apply a common bias signal to each line 612 and corresponding transducer element 610. Optionally, multiple biasing circuits 620 may be utilized to generate and apply corresponding bias signals to lines 612 and corresponding transducer elements 610. When multiple biasing circuits 620 are used, the biasing circuits 620 may separately generate bias signals having a common shape, amplitude and duration. Optionally, when multiple biasing circuits 620 are used, the biasing circuits 620 may separately generate bias signals that differ from one another in one or more of shape, amplitude and/or duration. Additionally or alternatively, it may be desirable to apply different bias signals to different sections of a transducer array, such as when the different sections of the transducer array have different shapes and/or receive different transmit signals.

The configuration of FIG. 6A allows a combination of bias circuits 620 to be implemented within the ultrasound system, without any modification to existing ultrasound probes.

Figure 6B:
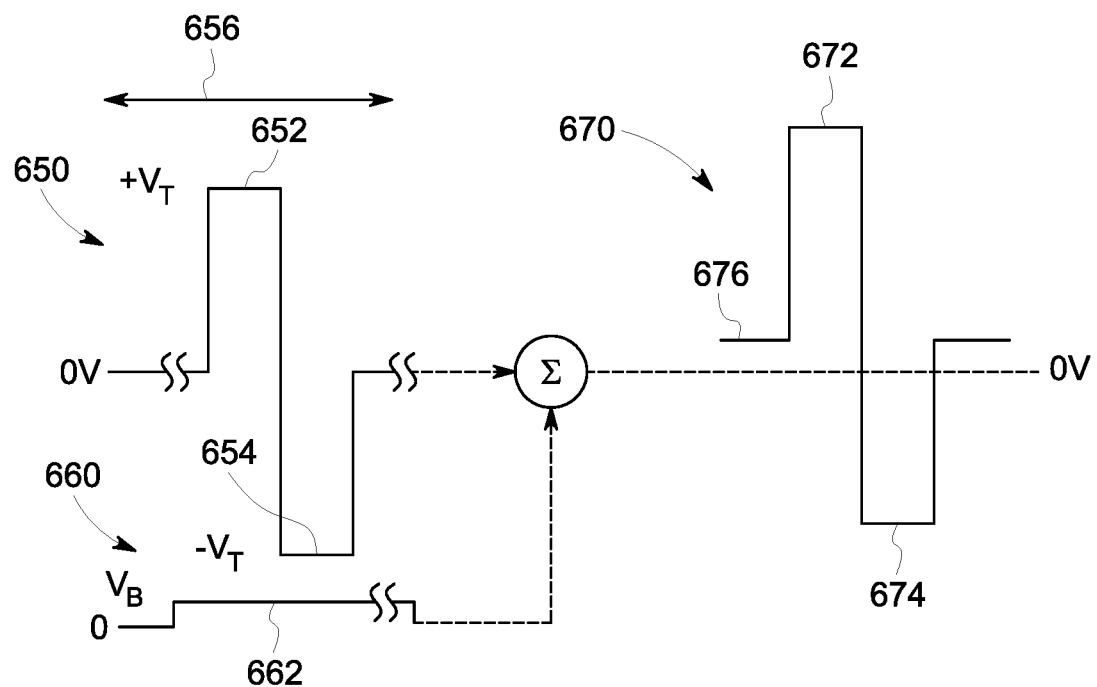
FIG. 6B illustrates an example of a transmit that may be transmitted during one transmit cycle in accordance with embodiments herein.

FIG. 6B illustrates an example of a transmit signal 650 that may be transmitted during one transmit cycle. The transmit signal 650 includes one or more pattern segments such as a first polarity segment 652 and a second polarity segment 654. The first and second polarity segments 652, 654 may include one or more pulses and/or may be interleaved with one another to collectively form a common pattern segment or separate pattern segments. For example, the transmit signal 650 may include a complex combination of positive and negative voltage pulses and/or waveform steps having different amplitudes. The first polarity segment 652 may be in the poling direction, while the second polarity segment 654 is in the opposite or depoling direction. Alternatively, the first polarity segment 652 may be in the depoling direction, while the second polarity segment 654 is in the poling direction. The term polarity segment is used generally to refer collectively to any/all portions of the transmit signal 650 during a transmit cycle that have a common polarity. In the present example, the first polarity segment 652 collectively refers to any and all portions of the transmit signal 650 during a transmit cycle that have a positive polarity, while the second polarity segment 654 collectively refers to any/all portions of the transmit signal 650 during a transmit cycle that have a negative voltage.

The transmit signal 650 in FIG. 6B represents a very simplified waveform that includes a single positive pulse in the first polarity segment 652 and a single negative pulse in the second polarity segment 654, that have peak voltages +/−$V_T$ (e.g., +/−60 V). The transmit signal 650 has a peak to peak range corresponding to the sum of the positive and negative peak voltages. The transmit and receive length 656 is substantially longer than the durations of the positive and negative pulses 652 and 654. For example, the transmit and receive time may have a period with a duration of 200 μs, whereas the positive and/or negative pulses have pulse widths of between 200 and 500 ns. The receive time is the time between two transmit signals where no voltage signals are sent to the probe. During the receive time the ultrasound system collects receive data (echoes) from the probe.

In accordance with embodiments herein, a bias signal 660 is generated (e.g., at the biasing circuit 620) that has a polarity that is the same as, and in a common direction with, the poling direction. For example, when the poling direction is positive, the bias signal will have a positive amplitude. Alternatively, when the poling direction is negative, the bias signal has a negative amplitude. The bias signal 660 has a constant bias amplitude $V_B$ that is limited to a relatively small percentage of the peak positive or peak negative pulse amplitude of the transmit signal. By way of example, the amplitude $V_B$ of the bias signal 660 may be less than 15% of the positive peak amplitude of the transmit signal (e.g., 1-9 V). Optionally, the amplitude $V_B$ of the bias signal 660 may be defined based on the "peak to peak" voltage range exhibited by the transmit signal 650. For example, the transmit signal 650 may include a positive peak amplitude +60 V and a negative peak amplitude of −60 V, thereby defining a peak to peak voltage range of 120 V. When defining the amplitude of the bias signal 660 in terms of the peak to peak amplitude, the bias signal amplitude may be an even smaller percentage, such as less than or equal to 5% of the peak to peak amplitude of the transmit signal. The bias signal 660 is maintained at a "high" level for a substantial majority of the duration of the transmit signal (e.g., continuously or over 90% of the 200 μs duration).

The bias signal 660 is merged with the transmit signal 650 to form a biased transmit signal 670 that includes a first biased polarity segment 672 and a second biased polarity segment 674. The bias transmit signal 670 is shifted to have a quiescent level 676 that is shifted in the the same direction as the poling direction by the amount corresponding to the amplitude of the bias signal 660. The biased transmit signal 670 is shifted in the direction of the poling direction but still includes both of positive and negative voltages over a transmit cycle. In this example, the first biased polarity segment 672 may extend in the poling direction, while the second biased polarity segment 674 may extend in the non-poling direction. The first biased polarity segment 672 has a peak amplitude corresponding to the sum of the amplitude of the peak positive transmit pulse and the amplitude of the bias signal (e.g., +$V_T$+$V_B$), while the second biased polarity segment 674 has a peak amplitude corresponding to the difference of the amplitude of the peak negative transmit pulse and the amplitude of the bias signal (e.g., −$V_T$+$V_B$). In the present example, the poling direction is in the positive direction and therefore, the first biased polarity segment 672 refers collectively to any/all portions of the biased transmit signal 670 that have a positive voltage, while the second biased polarity segment 674 refers collectively to any/all portions of the transmit signal 650 that have a negative voltage. Optionally, the first biased polarity segment 672 may extend in the non-poling direction, while the second biased polarity segment 674 may extend in the poling direction. The sequence of the first and second biased polarity segments 672 and 674 do not matter. The bias signal 660 may be limited to the length of the transmit pulse 656 or the bias signal 660 may extend for the entire pulse repetition time. For example, the bias signal 660 may be active during the entire transmit/receive period, or the bias signal 660 may be any length in-between.

The bias transmit signal 670 substantially eliminates the depoling in the transducer elements by shifting the transmit signal in the poling direction by the amount corresponding to the level of the bias signal. The shift corresponding to the bias signal is defined in terms of a ratio or relation to the voltage applied during transmit operations. In accordance with at least certain embodiments, the shift corresponding to the bias signal is maintained in a range of 2.5V to 10V, and more preferably in a range of 4-9V, and even more preferably in a range of 5-6V. For transmit operations that use a peak voltage of up to 30V, the bias signal may be up to 25% (and more preferably at or below 15%, and even more preferably at or below 10%) of the peak voltage of the transmit signal generated during a transmit cycle. For example, when the transmit voltage is varied between +/−60 V, the DC bias voltage was maintained at or below +/−9V, and more preferably at or below +/−6 V. By maintaining the level of the bias signal at a level between 2.5V to 10V, and more preferably 4-9V and even more preferably 5-6V, embodiments herein form a biased transmit signal having first and second biased polarity segments that substantially maintain amplitudes of the original transmit signal extending in the poling direction and in the non-poling direction, but shifted a small percentage in the poling direction. The foregoing bias transmit signal stabilizes the electrical dipole orientation of the composition within the transducer elements and thus avoid (or at least substantially diminish) depoling effects, while allowing implementation utilizing low voltage biasing circuitry.

Further, the bias signal 662 is defined to have a pulse width that is relatively long as compared to a length of the poling segments (e.g., 652, 654) of the transmit signal, thereby further stabilizing the electrical dipole orientation of the transducer material. For example, the DC bias signal may be maintained continuously throughout an entire transmit and receive cycle and/or maintained for a substantial majority of the transmit and receive cycle (e.g., 90% or more).

Figure 7:
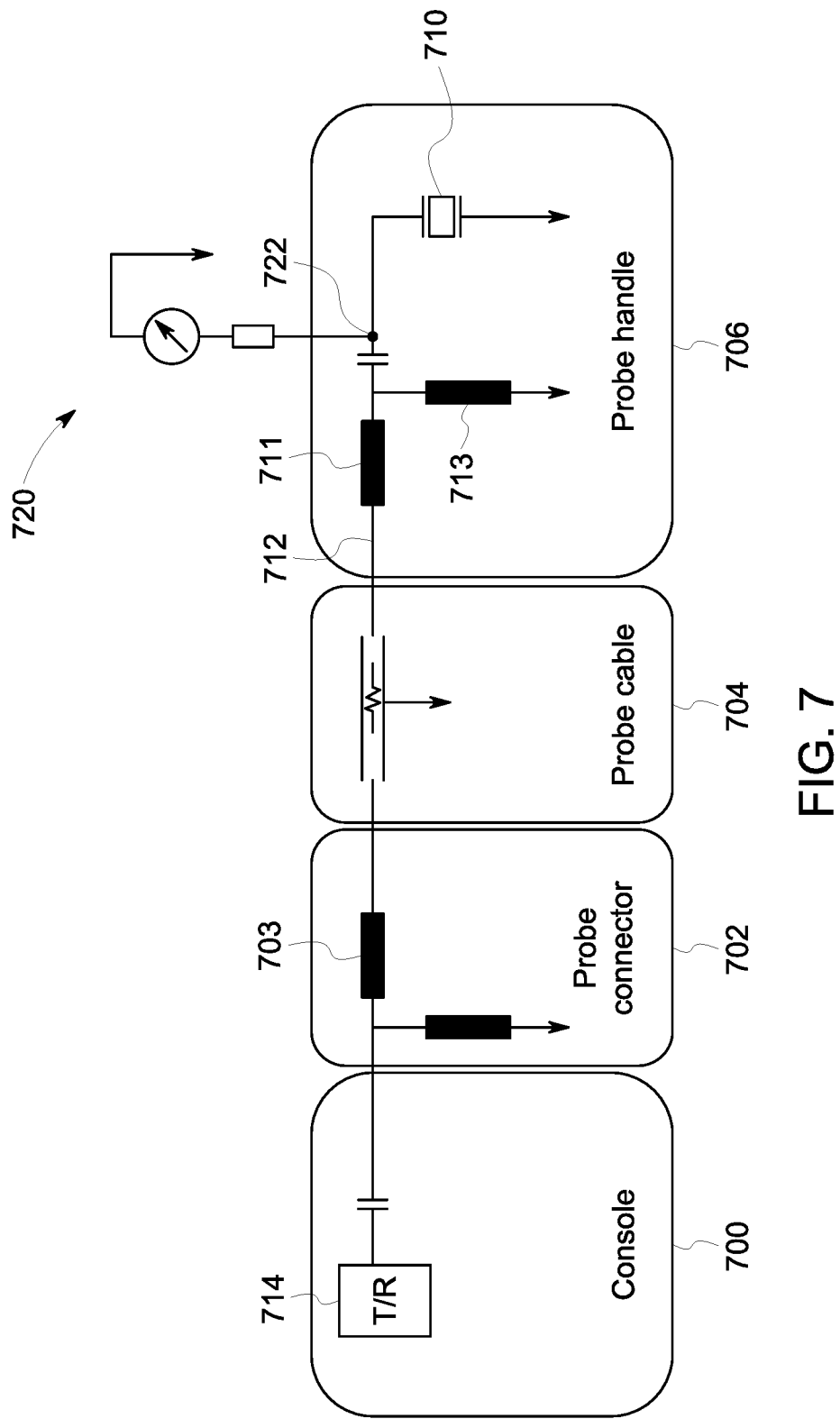
FIG. 7 illustrates a block diagram of an ultrasound system including a DC bias circuit implemented in accordance with embodiments herein.

FIG. 7 illustrates a block diagram of an ultrasound system including a DC bias circuit implemented in accordance with embodiments herein. The ultrasound system includes a console 700 that is connected to a probe connector 702. The console 700 may include all or a portion of the components described and illustrated in connection with one or more of FIGS. 1-4. The probe connector 702 is provided on a proximal end of a probe cable 704. A distal end of the probe cable 704 is connected to a probe 706. A line 712 electrically connects a transducer element 710 to corresponding contacts (not shown) in the probe connector 702. An inductor combination 711, 713 is provided within the probe 706. An inductor 703, within the probe connector 702, is also provided along line 712. The probe cable 704 is connected at the probe connector 702 to a transmit/receive (T/R) circuit 714 within the console 700.

During transmit operations, the T/R circuit 714 delivers a transmit signal to cause the transducer element 710 to transmit ultrasound signals. During receive operations, the T/R circuit 714 records return "echo" signals along line 712 corresponding to ultrasound echo waves sensed at the transducer element 710. A biasing circuit 720 is connected at node 722 within the probe 706. The biasing circuit 720 is configured to introduce a bias signal, such as a DC bias voltage, onto the line 712. The bias signal is superimposed at node 722 onto the transmit signal generated by the transmit/receive circuit 714. The configuration of FIG. 7 allows the biasing circuit 720 to be implemented within each individual probe 706, thereby avoiding any need for modification to conventional consoles for ultrasound systems. Furthermore, the configuration of FIG. 7 is possible if parallel inductors between transmit/receive line and ground are used in probe handle or probe connector.

Optionally, the embodiment of FIG. 7 (as well as other embodiments herein) may be implemented in connection with wireless probes where the bias circuitry is implemented within the probe handle.

Figure 8:
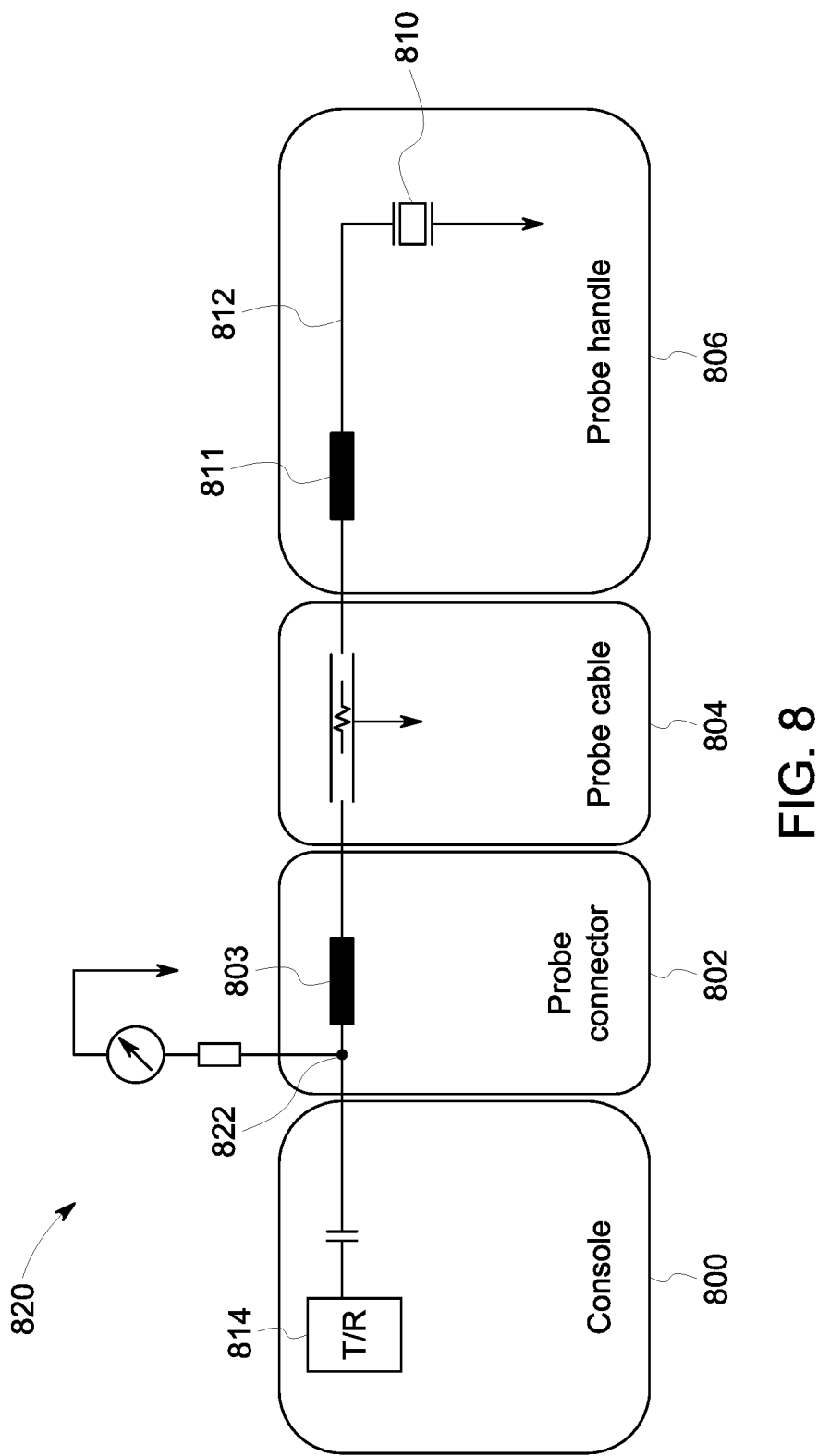
FIG. 8 illustrates a block diagram of an ultrasound system including a DC bias circuit implemented in accordance with embodiments herein.

FIG. 8 illustrates a block diagram of an ultrasound system including a DC bias circuit implemented in accordance with embodiments herein. The ultrasound system includes a console 800 that is connected to a probe connector 802. The console 800 may include all or a portion of the components described and illustrated in connection with one or more of FIGS. 1-4. The probe connector 802 is provided on a proximal end of a probe cable 804. A distal end of the probe cable 804 is connected to a probe 806. A line 812 electrically connects a transducer element 810 to corresponding contacts (not shown) in the probe connector 802. An inductor 811 is provided within the probe 806, and an inductor 803 is provided within the probe connector 802 along line 812. The probe cable 804 is connected at the probe connector 802 to a transmit/receive (T/R) circuit 814 within the console 800.

During transmit operations, the T/R circuit 814 delivers a transmit signal to cause the transducer element 810 to transmit ultrasound signals. During receive operations, the T/R circuit 814 records return "echo" signals along line 812 corresponding to ultrasound echo waves sensed at the transducer element 810. A biasing circuit 820 is connected at node 822 within the probe connector 802. The biasing circuit 820 is configured to introduce a bias signal, such as a DC bias voltage, onto the line 812. The bias signal is superimposed at node 822 onto the transmit and receive line. The configuration of FIG. 8 allows the biasing circuit 820 to be implemented within the probe connector 802, thereby avoiding any need for modification to conventional consoles for ultrasound systems and potentially to an existing design for the internal components of the probe body.

Figure 9:
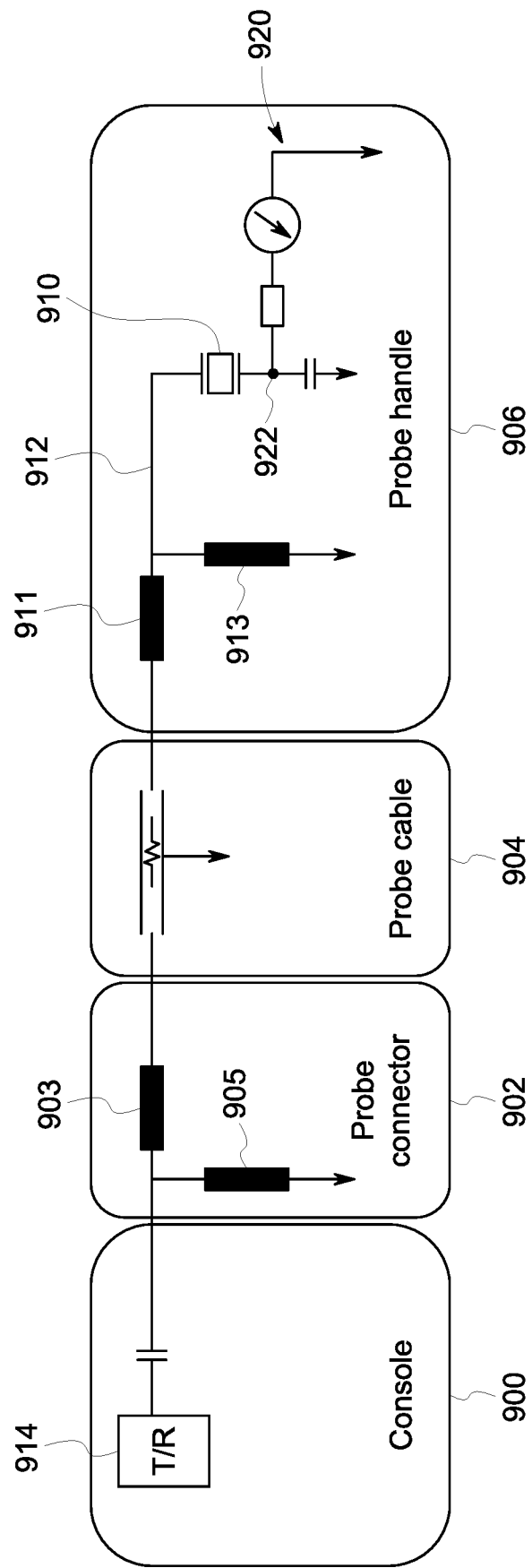
FIG. 9 illustrates a block diagram of an ultrasound system including a DC bias circuit implemented in accordance with embodiments herein.

FIG. 9 illustrates a block diagram of an ultrasound system including a DC bias circuit implemented in accordance with embodiments herein. The ultrasound system includes a console 900 that is connected to a probe connector 902. The console 900 may include all or a portion of the components described and illustrated in connection with one or more of FIGS. 1-4. The probe connector 902 is provided on a proximal end of a probe cable 904. A distal end of the probe cable 904 is connected to a probe 906. A line 912 electrically connects a transducer element 910 to corresponding contacts (not shown) in the probe connector 902. An inductor combination 911, 913 is provided within the probe 906, and an inductor combination 903, 905 is provided within the probe connector 902. The inductor combination may include one or multiple parallel inductors and/or one or multiple series in inductors. In at least one embodiment, the inductor combination may include 2 parallel inductors or 2 series inductors. The probe cable 904 is connected at the probe connector 902 to a transmit/receive (T/R) circuit 914 within the console 900.

During transmit operations, the T/R circuit 914 delivers a transmit signal to cause the transducer element 910 to transmit ultrasound signals. During receive operations, the T/R circuit 914 records return "echo" signals along line 912 corresponding to ultrasound echo waves sensed at the transducer element 910. A biasing circuit 920 is connected at node 922 within the probe 906 between the transducer element 910 and ground. The biasing circuit 920 is configured to introduce a bias signal, such as a DC bias voltage, onto the line 912. The ground potential of the transducer is shifted by the DC-bias. The bias signal is superimposed at node 922 onto the ground voltage level. The configuration of FIG. 9 allows the biasing circuit 920 to be implemented within the probe connector 902, thereby avoiding any need for modification to conventional consoles for ultrasound systems. Furthermore, the configuration of FIG. 9 is possible if parallel inductors between transmit/receive line and ground are used in probe handle or probe connector. The ground potential of the transducer is often connected to many or all elements in parallel. Therefore, the configuration of FIG. 9 does not require a modification of each transmit/receive line and is easier to implement.

Optionally, the embodiment of FIG. 9 (as well as other embodiments herein) may be implemented in connection with wireless probes where the bias circuitry is implemented within the probe handle.

From the foregoing examples in FIGS. 6A-9, it is seen that the biasing voltage can be generated and introduced after the AC coupled beamformer, at the probe connector, within the probe upstream of the transducer element, within the probe downstream of the transducer element as well as elsewhere. In the embodiments of FIGS. 7 and 8, the bias signal is applied to each line that carries a corresponding transmit signal. In the embodiment of FIG. 9, the ground connection can be DC decoupled on the transducer and the bias signal applied as an inverse voltage to the transducer ground.

In accordance with aspects herein, embodiments increase stability of depolarization. In accordance with aspects herein, embodiments enable a relatively low bias voltage to be utilized (<10V approximately <1 kV/cm) and does not necessarily lead to unipolar signals, but instead biased bipolar signals. In accordance with aspects herein, embodiments achieve a substantial increase in depolarization stability when biasing voltages are applied to binary SC materials (e.g., PMN-PT). In accordance with aspects herein, several unexpected results were found. First, it was unexpected to find that a low DC bias achieved the same or better depoling performance as substantially higher voltage bias signals for binary single crystal material (binary SC). Further, it was unexpected to find that a low voltage bias signal does work to some degree with ternary single crystal (ternary SC), but not as well as the low voltage bias signal works with binary single crystal material. Further, it was unexpected to find the low voltage bias signal stabilizes the weaker binary SC material to voltages equal or beyond the capability of ternary SC materials.

Tests were conducted to study the depoling effect exhibited by piezoelectric substrates formed from certain types of single crystal materials. The test analyzed different transducers. In connection with the test, various transducers were excited with different transmit patterns that were combined with bias signals having different voltage levels. Some of the test results are shown in the following Figures.

Figure 10:
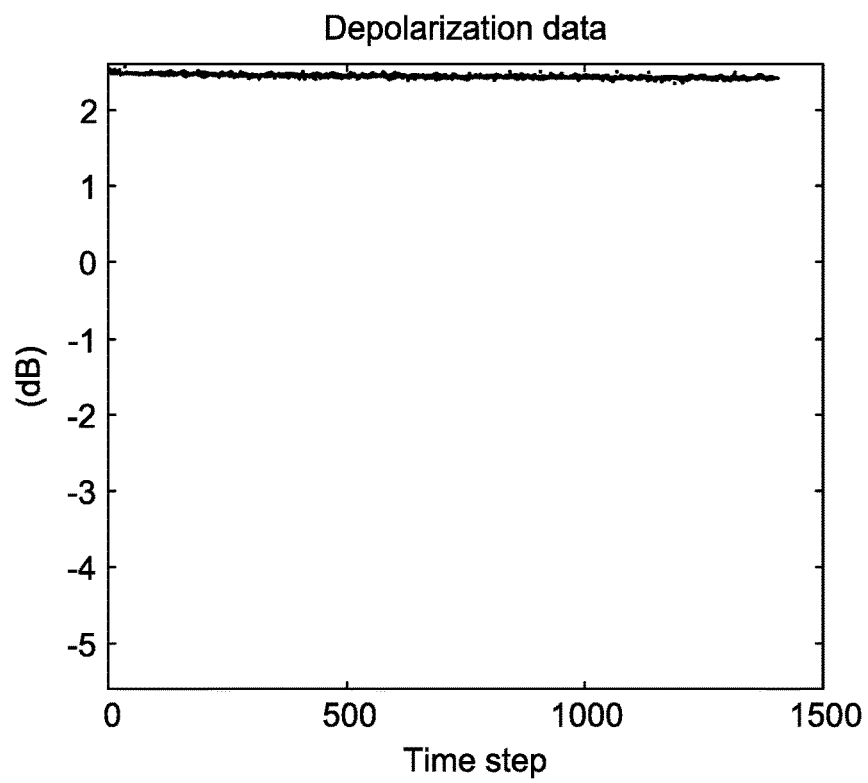
FIG. 10 illustrates the test with applied DC-bias results collected in connection with one type of transducer in accordance with embodiments herein.

FIG. 10 illustrates the test results collected in connection with one type of transducer that utilized binary single crystal materials, with sensitivity indicated in decibels along the vertical axis and a time of operation indicated along the horizontal axis. In connection with the measurement, the transducer elements were excited with a transmit signal having a desired pattern, along with a bias signal having a 5V DC steady-state amplitude. The transmit signal included one or more positive segments having a peak positive amplitude >60 V and one or more negative segments having a peak negative amplitude of >−60 V. When combining the bias signal with the transmit signal, the resulting biased transmit signal which shifted in the direction of the poling direction of the transducer elements by a 5V DC steady-state amplitude. The biased transmit signal was applied to the transducer elements for a total operating time of several hours. Periodically, throughout operation, a sensitivity of the transducer elements was measured to compare the ratio of the input and output power levels. As illustrated in FIG. 10, the sensitivity remained stable at between 2 dB and 3 dB over the hours of operation.

Figure 11:
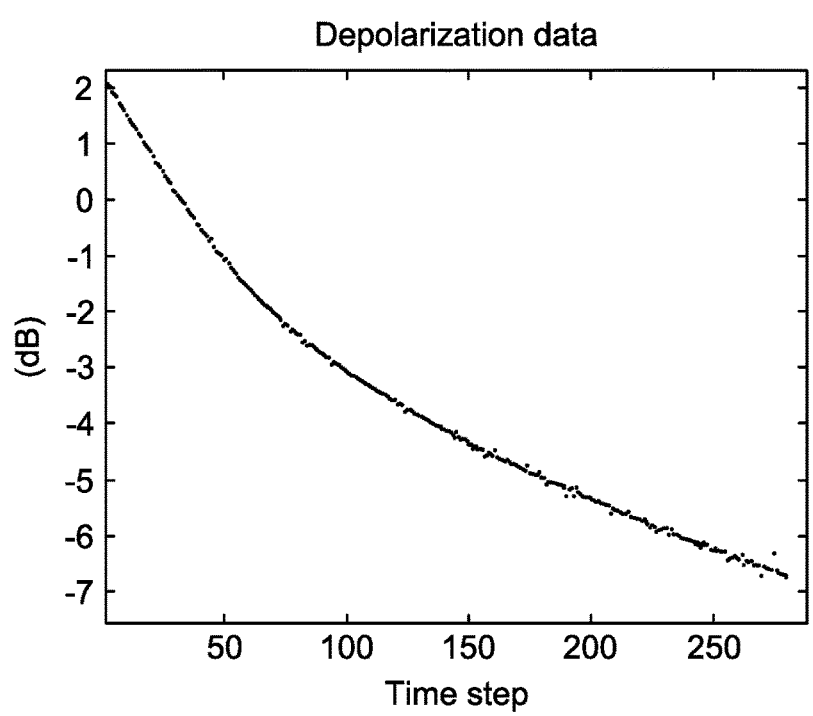
FIG. 11 illustrates the test results without DC-bias collected in connection with the same type of transducer as tested in connection with FIG. 10 in accordance with embodiments herein.

FIG. 11 illustrates the test results collected in connection with the same type of transducer as tested in connection with FIG. 10, with sensitivity indicated in decibels along the vertical axis and a time of operation indicated along the horizontal axis. In connection with the measurement, the transducer elements were excited with a transmit signal having the same transmit pattern as applied in connection with the test of FIG. 10, but with no bias signal (e.g., a bias signal was set to 0V) added to the transmit signal. The test results in FIG. 11 indicate the sensitivity of the transducer over the test period of operation when a non-biased transmit signal is applied alone. The transmit signal was applied to the transducer elements for a total operating time of several minutes. Periodically, throughout the minutes of operation, a sensitivity of the transducer elements was measured to compare the ratio of the input and output power levels. As illustrated in FIG. 11, the sensitivity dropped from an initial level at slightly less than 3 dB at a relatively sharp rate. In the first 10 minutes, the sensitivity had dropped to a −3 dB, at approximately 20 minutes, the sensitivity had dropped to −5 dB and at 30 minutes, the sensitivity was approaching a −7 dB.

From the foregoing tests of FIGS. 10 and 11, it is clear that application of a bias signal in a direction of the poling direction of the transducer elements stabilizes the transducer over a period of several hours of operation.

Figure 12:
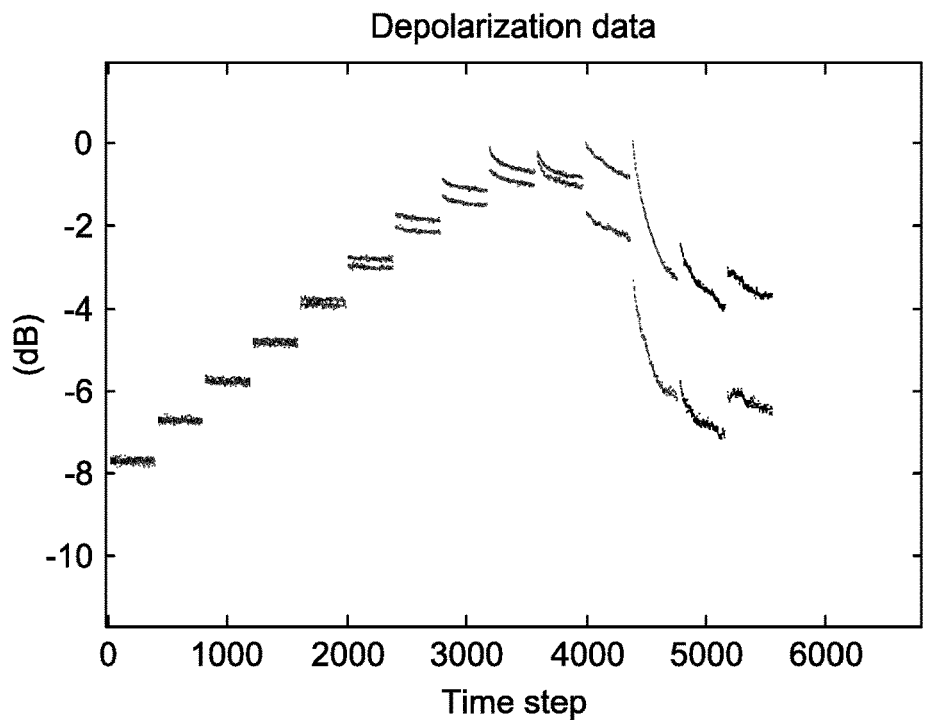
FIG. 12 illustrates test results without DC-bias collected in connection with one type of transducer in accordance with embodiments herein.

FIG. 12 illustrates test results collected in connection with one type of transducer that utilized binary single crystal materials, with sensitivity indicated in decibels along the vertical axis and a time of operation indicated along the horizontal axis. During the test, the transducer was excited with a transmit signal that utilized harmonic pulse inversion, but with no bias signal (e.g., a bias signal was set to 0 V) added to the transmit signal. A series of horizontal measurement lines are illustrated, each of which corresponds to a few minutes of measurement cycle. During each measurement cycle, a particular voltage level was utilized for the transmit signal, with different voltage levels applied during different measurement cycles. For example, the transmit voltage was started at approximately 25 V and was increased in steps during each measurement cycle until reaching 120 V. The sensitivity measurements during the first 2-3 hours remained relatively constant. However, after 3-4 hours of operation, the sensitivity begins to drop during the measurement cycles.

Figure 13:
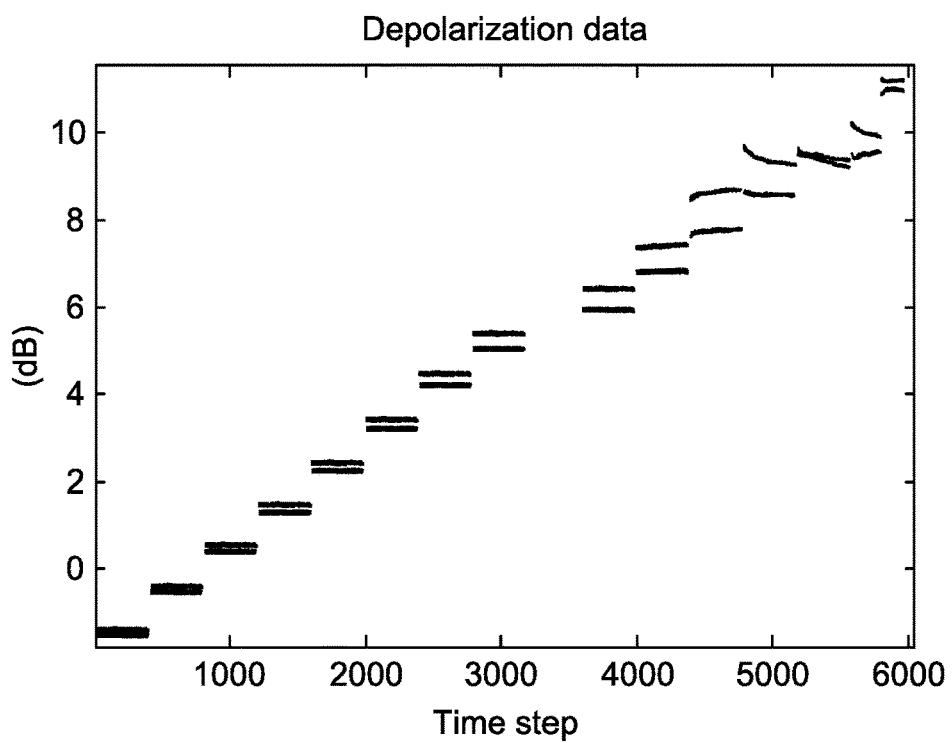
FIG. 13 illustrates test results with applied DC-bias collected in connection with the same type of transducer as used in the test results for FIG. 12 in accordance with embodiments herein.

FIG. 13 illustrates test results collected in connection with the same type of transducer as used in the test results for FIG. 12, with sensitivity indicated in decibels along the vertical axis and a time of operation indicated along the horizontal axis. During the test, the transducer was excited with the same type of transmit signal and with the same transmit voltage steps as utilized in FIG. 12, along with a bias signal having a 10 V DC steady-state amplitude. A series of horizontal measurement lines are illustrated, each of which corresponds to a measurement cycle of several minutes. During each measurement cycle, a particular corresponding voltage level was utilized for the transmit signal, with different voltage levels applied during different measurement cycles.

From the test results of FIGS. 12-13, it can be seen that the application of a bias signal in a direction of the poling direction of the transducer elements stabilizes the transducer elements at higher transmit voltages. For example, up to 6 dB higher transmit voltage may be utilized without the transducer elements exhibiting the depoling effects.

Repolarization Implementations

As explained in accordance with embodiments herein, by applying a low voltage bias signal during transmit operations, methods and systems herein are able to stabilize transducers to limit or avoid a depoling effect. However, in some instances, a certain amount of depoling may still be experienced. For example, higher transmit voltages may be applied in order to achieve certain levels of image quality. At higher transmit voltages, a certain amount of depoling may still occur. It is recognized that a depoling effect may occur due to various factors, not simply through extended use over time or through the use of high transmit voltages. For example, a depoling effect may occur when a probe is stored at an excessive temperature. When a depoling effect occurs, in the past, it was not possible to completely reverse the depoling effect (repoling) through an ultrasound imaging system console. Instead, the conventional approach required the probe to go through a refurbishment process, in which the probe is sent to a refurbishment facility and connected to a separate refurbishment machine (not an ultrasound console) specifically designed to deliver high voltages to the probe. The voltage delivered to a probe during a refurbishment process is substantially higher than voltage levels utilized during ultrasound imaging transmit operations. The ultrasound console of an ultrasound imaging system does not have the ability to operate at the high voltage levels that are utilized by a separate refurbishment machine. For example, a refurbishment machine may deliver a voltage of 150 V or higher during a refurbishment process to repolarize transducer elements. Alternatively, the probe can be disassembled during refurbishment to repole with lower DC voltages. This is not possible with fully assembled probes if parallel inductors are used in the probe connector or probe handle.

In accordance with new and unique aspects herein, it has been found that transducer elements may be repoled to reverse the effects of depoling by applying a repoling signal having a voltage that is lower or similar to the voltage applied during transmit operations, when the ultrasound system also combines a bias signal with the transmit signal to form a biased transmit signal that is shifted in the poling direction. Embodiments herein are able to achieve repoling, even when a transducer element exhibits substantially complete depolarization. In accordance with new and unique aspects herein, the methods and systems described herein achieve good results of repolarization in connection with binary single crystal materials, as well as with other transducer materials (e.g., ternary single crystal). For example, a relatively long electrical pulse (e.g., up to several seconds) may be emitted from the ultrasound console and used to repolarize a transducer array, such as in connection with configurations that utilize parallel inductors. A combination of a low voltage DC bias and active repolarization signal allows a higher transmit voltage to be utilized (without concerns for the depoling effect) which increases image quality. The higher transmit voltages are now available given that repolarization may be implemented within the ultrasound console and/or within the probe to allow a probe to be repaired in the field. Embodiments herein allow transducer arrays to be driven, during transmit operations, at higher voltages, thereby increasing image quality, even though the higher voltages may result in the transducer elements approaching the poling limits, given that the repolarization signals and patterns described herein are able to return the condition of the probe to at or near the original polarization level.

Embodiments herein may implement repoling methods and circuits in connection with a variety of ultrasound transducers without limitation on a geometry of the transducer. However, repoling implementations herein may have better suitability in connection with transducers that are made from materials susceptible to depoling, including (but not limited to) single crystal materials and the like. In particular, repoling embodiments herein are well-suited to at least partially (and preferably substantially) revert a depoling effect exhibited by one or more transducer elements that are constructed substantially from binary or ternary single crystal materials or having a substantially homogeneous composition of binary single crystal materials. The lower coercive field strength of single crystal materials, compared to traditional PZTs, leads to a higher risk for depoling. Repoling embodiments may be implemented in connection with ultrasound probes having various types and arrangements of transducers that are configured to collect any and all types of ultrasound data sets, including (but not limited to) B-mode data, power Doppler data, Doppler data, strain data, two-dimensional data, three-dimensional data, four dimensional data, shear wave data or otherwise, as described herein and as described in the patents, patent applications and other publications referenced and incorporated herein.

Figure 14A:
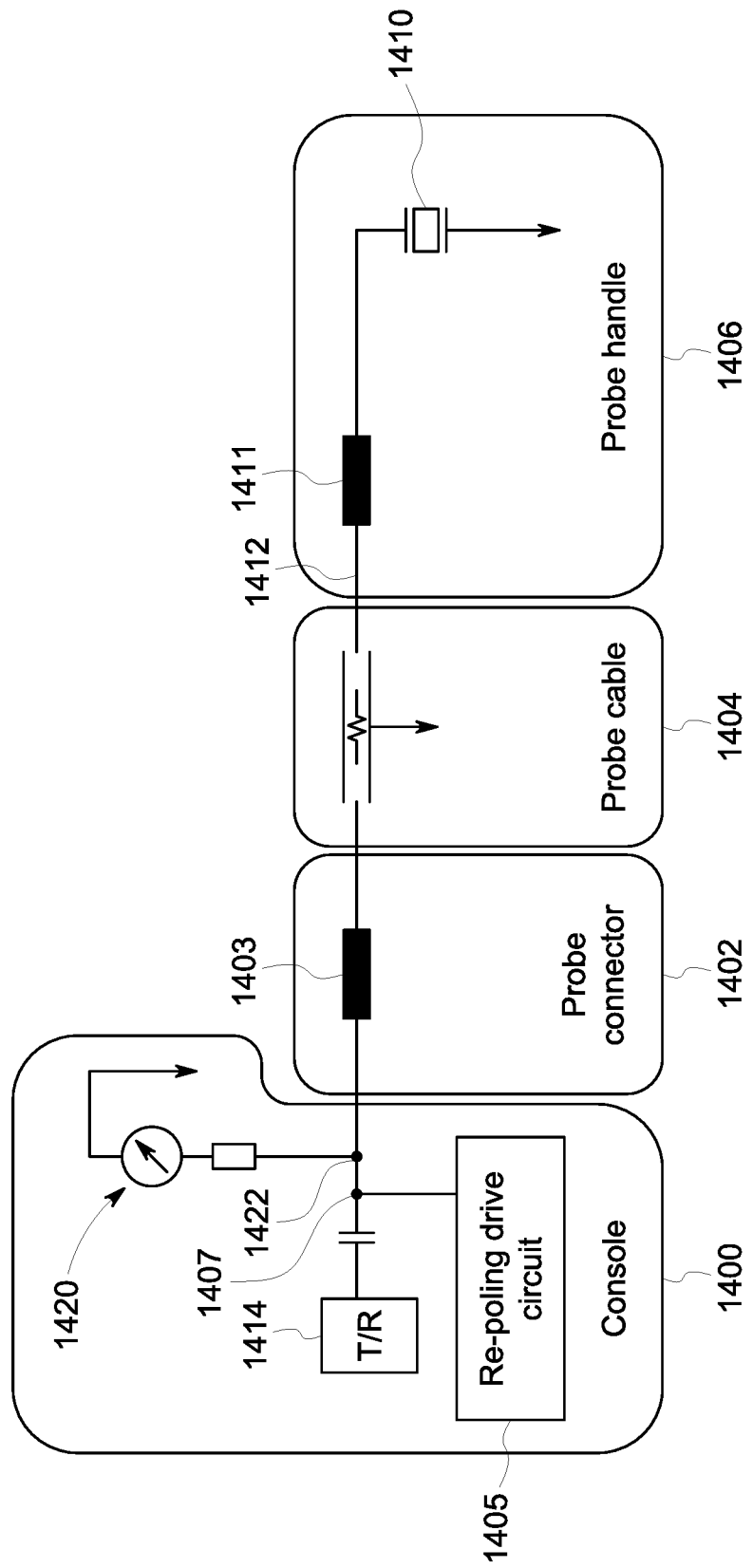
FIG. 14A illustrates a block diagram of an ultrasound system including a DC bias circuit and a repoling drive circuit implemented in accordance with embodiments herein.

FIG. 14A illustrates a block diagram of an ultrasound system including a DC bias circuit and a repoling drive circuit implemented in accordance with embodiments herein. The ultrasound system includes a console 1400 that is connected to a probe connector 1402. The console 1400 may include all or a portion of the components described and illustrated in connection with one or more of FIGS. 1-4. The probe connector 1402 is provided on a proximal end of a probe cable 1404. A distal end of the probe cable 1404 is connected to a probe 1406. A transmit line 1412 electrically connects a transducer element 1410 to corresponding contacts (not shown) in the probe connector 1402. The probe connector 1402 is configured to be mated with a mating connector provided on the console (not shown). An inductor 1411, within the probe 1406, and an inductor 1403, within the probe connector 1402, are provided along line 1412. The probe cable 1404 is connected at the probe connector 1402 to a transmit/receive (T/R) circuit 1414 within the console 1400. In the example of FIG. 14A, the transmit line 1412 may also be utilized as a receiver line to convey receive signals from the transducer element to the transceiver 1414. Optionally, separate transmit and receive lines may be utilized. A capacitor is provided between the T/R circuit 1414 and the node 1422.

During transmit operations, the T/R circuit 1414 delivers a transmit signal to cause the transducer element 1410 to transmit ultrasound signals. During receive operations, the T/R circuit 1414 records return "echo" signals along line 1412 corresponding to ultrasound echo waves sensed at the transducer element 1410. A biasing circuit 1420 is connected at node 1422 within the console 1400. The biasing circuit 1420 is configured to introduce a bias signal, such as a DC bias voltage, onto the line 1412. The bias signal is superimposed at node 1422 onto the transmit signal generated by the transmit/receive circuit 1414.

In accordance with new and unique aspects herein, the ultrasound system further includes a repoling signal. In accordance with some embodiments herein, the repoling signal is generated by a repoling drive circuit 1405. The repoling drive circuit 1405 is connected to the transmit line 1412 at node 1407. The repoling drive circuit 1405 is configured to generate a repoling signal having a repoling pattern configured to at least partially revert the depoling effect exhibited by one or more transducer elements 1410. In the example of FIG. 14A, the transmit/receive circuit 1414 is implemented as a drive circuit separate and distinct from the repoling drive circuit 1405 and the biasing circuit 1420 to provide distinct drive circuits. Alternatively, as explained herein, a common drive circuit may be configured to provide i) transmit drive signals, in connection with beamforming, ii) repoling signals and/or iii) biasing signals, or any combination thereof. For example, the T/R circuit 1414 may also generate the repoling signal, while the biasing circuit 1420 remains separate. Alternatively, the T/R circuit 1414 may also generate the biasing signal, while the repoling drive circuit remains separate. Alternatively, the T/R. circuit 1414 may generate all three, transmit signals, repoling signals and biasing signals. The biasing circuit 1420 generates the bias signal contemporaneous in time with the transmit signal such that the bias signal is combined with the transmit signal to form the biased transmit signal that is shifted in the poling direction. The biasing circuit 1420 further generates the bias signal contemporaneous in time with the repoling signal such that the bias signal is combined with the repoling signal to form a biased repoling signal that is also shifted in the poling direction.

The repoling signal may deliver an active repoling pattern at various times and, as one example, may be used during normal scanning sequences. For example, a repoling signal may be applied at the end of a series of transmit/receive operations that collect an ultrasound image frame. Additionally or alternatively, the repoling signal may be applied at particular times during a scanning sequence, such as when an operator places an ultrasound system in a freeze mode.

In the present example, a common biasing circuit 1420 is utilized in connection with the T/R circuit 1414 and the repoling drive circuit 1405. The common biasing circuit 1420 may add a common bias signal to both of the transmit signals and repoling signals. Alternatively, the common biasing circuit 1420 may add a first bias signal to transmit signals and a different second bias signal to repoling signals. Alternatively, a first biasing circuit 1420 may be utilized with the T/R circuit 1414, and a separate second biasing circuit (not shown) may be utilized in connection with the repoling drive circuit 1405. When separate first and second biasing circuits 1420 are implemented with the corresponding T/R circuit 1414 and repoling drive circuit 1405, the first and second biasing circuits 1420 may introduce a common bias signal into the transmit and repoling signals, or alternatively introduce different first and second bias signals into the respective ones of the transmit and repoling signals.

Figure 14B:
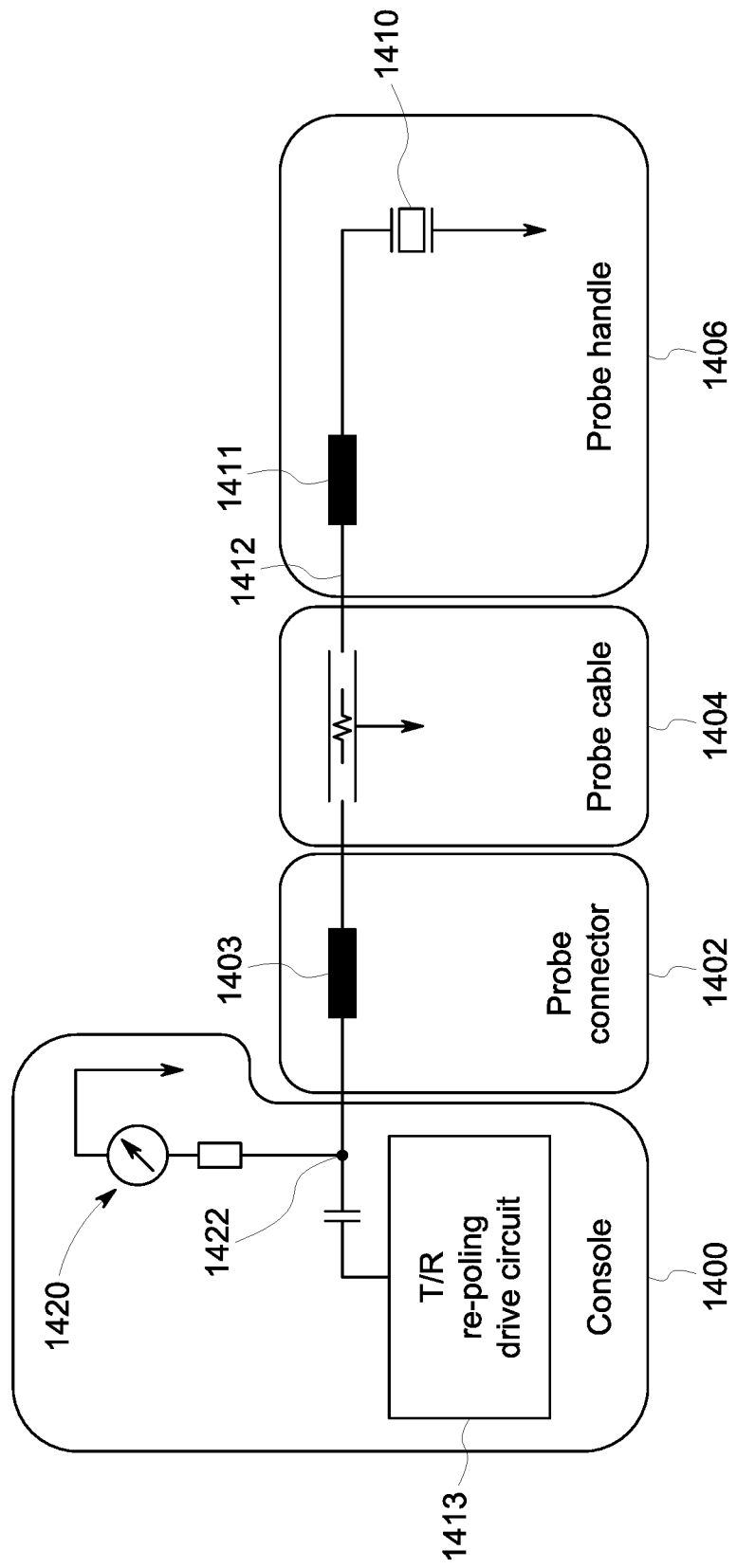
FIG. 14B illustrates a block diagram of an ultrasound system including a DC bias circuit and a repoling drive circuit implemented in accordance with an alternative embodiment herein.

FIG. 14B illustrates a block diagram of an ultrasound system including a DC bias circuit and a repoling drive circuit implemented in accordance with an alternative embodiment herein. In the embodiment of FIG. 14B, the transmit/receive circuit 1413 is also configured to operate as the repoling drive circuit, thereby providing a common drive circuit to generate both transmit signals and repoling signals. Other components within the ultrasound system of FIG. 14B are the same as in FIG. 14A, and therefore the description is not repeated hereafter.

FIGS. 14A and 14B illustrate simplified diagrams associated with a single transducer element 1410, although it is understood that the probe 1406 will include a transducer array with multiple transducer elements 1410, multiple lines 1412, and multiple T/R circuits 1414, 1413. In some configurations, a separate T/R circuit 1414, 1413 may be provided for each line 1412 and each transducer element 1410. Alternatively, a subset Y of the transducer elements 1410 may be coupled to a common line 1412 and a common T/R circuit 1414 (e.g., in connection with two-dimensional transducer arrays having a relatively large number of transducer elements). In connection with the configuration of FIG. 14B, a common drive circuit 1414 is implemented for the T/R functionality and repoling functionality for a single line 1412, all lines 1412 and/or a subset of the lines 1412.

In connection with the configuration of FIG. 14A, separate repoling drive circuits 1405 may be provided for each line 1412. Alternatively, a common repoling drive circuit 1405 may be coupled to all of the lines 1412 and all of the transducer elements 1410, with lines 1412 and elements 1420 selected individually or in groups. Alternatively, subsets of the transducer elements 1410 may be coupled to a common line 1412 and a corresponding repoling drive circuit 1405. For example, a number N of repoling drive circuits 1405 may be provided, with each repoling drive circuit coupled to a subset of M transducer elements, thereby allowing a smaller group of N repoling drive circuits 1405 to revert a depoling effect for a larger number of NxM transducer elements.

In accordance with embodiments herein, a common biasing circuit 1420 may generate and apply a common bias signal to each line 1412 and corresponding transducer element 1410. The common biasing circuit 1420 may also be utilized in connection with transmit signals from multiple T/R circuits 1414 and/or one or more repoling drive circuits 1405. Optionally, multiple biasing circuits 1420 may be utilized to generate and apply corresponding bias signals to lines 1412 and corresponding transducer elements 1410. When multiple biasing circuits 1420 are used, the biasing circuits 1420 may separately generate bias signals having a common shape, amplitude and duration. Optionally, when multiple biasing circuits 1420 are used, the biasing circuits 1420 may separately generate bias signals that differ from one another in one or more of shape, amplitude and/or duration. Additionally or alternatively, it may be desirable to apply different bias signals to different sections of a transducer array, such as when the different sections of the transducer array have different shapes and/or receive different transmit signals.

The configurations of FIGS. 14A and 14B allow one or more bias circuits 1420, and/or repoling circuits 1405 to be implemented within the ultrasound system, without any modification to existing ultrasound probes. The configuration of FIG. 14B also allows T/R circuits 1413 within the ultrasound system to be reconfigured to deliver repoling signals between transmit signals without any modification to existing ultrasound probes.

Figure 14C:
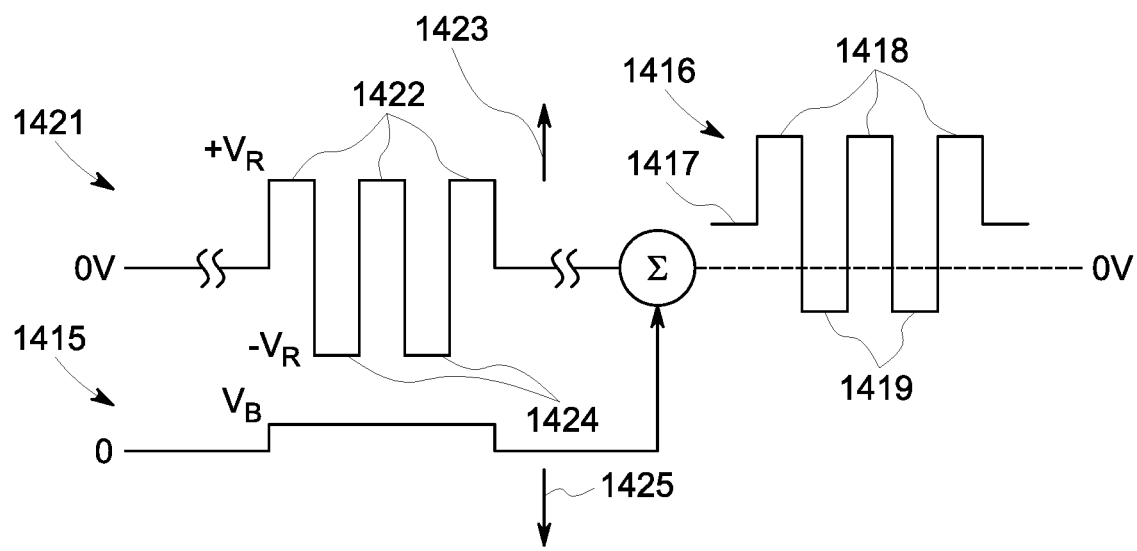
FIG. 14C illustrates an example of a repoling signal that may be transmitted during repoling cycles between successive transmit cycles.

FIG. 14C illustrates an example of a repoling signal 1421 that may be transmitted during repoling cycles between successive transmit cycles. The repoling signal 1421 includes a series of pulses, representing a pattern segment, having a first polarity segment 1422 and a series of pulses having a second polarity segment 1424. The first and second polarity segments 1422, 1424 may be part of a common pattern segment or represent separate pattern segments. The first and second polarity segments 1422, 1424 include one or more pulses and/or may be interleaved with one another. For example, the repoling signal 1421 may include a complex combination of positive and negative voltage pulses and/or waveform steps having different amplitudes. The first polarity segment 1422 may be in the poling direction 1423, while the second polarity segment 1424 is in the opposite or depoling direction 1425. In the present example, the first polarity segment 1422 includes more pulses than the second polarity segment 1424 such that the repoling signal begins and ends with pulses in the poling direction 1423. Alternatively, the first pulse in the repoling signal 1421 may begin in the depoling direction 1425, while the last pulse in the repoling signal 1421 extends in the poling direction 1423.

Alternatively, the first polarity segment 1452 may extend in the depoling direction, while the second polarity segment 1454 extends in the poling direction.

The term "polarity segment" is used generally to refer collectively to any/all portions of the repoling signal 1421 during a repoling cycle that have a common polarity. In the present example, the first polarity segment 1422 collectively refers to any and all pulses of the repoling signal 1421 during a repoling cycle that have a positive polarity, while the second polarity segment 1424 collectively refers to any/all pulses of the repoling signal 1421 during a repoling cycle that have a negative voltage. The repoling signal 1421 in FIG. 14C represents a simplified waveform that includes a series of three positive pulses in the first polarity segment 1422 and a series of two negative pulses in the second polarity segment 1424, that have peak voltages+/−VR. The repoling signal 1421 has a peak to peak range corresponding to the sum of the positive and negative peak voltages.

In accordance with embodiments herein, a bias signal 1415 is generated (e.g., at the biasing circuit 620, 820, 1420) that has a polarity that is the same as, and in a common direction with, the poling direction 1423. The bias signal 1415 may be the same bias signal as 660 combined with the transmit signal 650, or different. For example, when the poling direction is positive, the bias signal will have a positive amplitude. Alternatively, when the poling direction is negative, the bias signal has a negative amplitude. The bias signal 1415 has a bias amplitude $V_B$ that is defined based on one or both of the transmit signal and/or the repoling signal. For example, the amplitude of the bias signal 1415 may be defined as a percentage of the amplitude of the transmit signal. Additionally or alternatively, the amplitude of the bias signal 1415 may be defined as a percentage of the amplitude of the repoling signal. Additionally or alternatively, the amplitude of the bias signal 1415 may be defined by subtracting a predetermined offset from the amplitude of the transmit signal (e.g., transmit voltage—X volts). Additionally or alternatively, the amplitude of the bias signal 1415 may be defined by subtracting a predetermined offset from the amplitude of the repoling signal (e.g., repoling voltage—X volts). Additionally or alternatively, the bias signal 1415 may be defined based on both of the transmit and repoling signals. For example, the amplitude of the bias signal may be defined based on an average of the amplitudes of the transmit and repoling signals.

The bias signal 1415 is merged with the repoling signal 1421 to form a biased repoling signal 1416 that includes a first biased polarity segment 1418 and a second biased polarity segment 1419. The bias repoling signal 1416 is shifted to have a quiescent level 1417 that is shifted in the same direction as the poling direction by the amount corresponding to the amplitude of the bias signal 1415. The biased repoling signal 1416 is shifted in the direction of the poling direction but still includes both of positive and negative voltages over a repoling cycle. In this example, the first biased polarity segment 1418 may extend in the poling direction, while the second biased polarity segment 1419 may extend in the non-poling direction. The first biased polarity segment 1418 has a peak amplitude corresponding to the sum of the amplitude of the peak positive repoling pulse and the amplitude of the bias signal (e.g., $+V_T+V_B$), while the second biased polarity segment 1419 has a peak amplitude corresponding to the difference of the amplitude of the peak negative repoling pulse and the amplitude of the bias signal (e.g., $-V_T+V_B$). In the present example, the poling direction is in the positive direction and therefore, the first biased polarity segment 1418 refers collectively to any/all portions of the biased repoling signal 1416 that have a positive voltage, while the second biased polarity segment 1419 refers collectively to any/all portions of the repoling signal 1421 that have a negative voltage. Optionally, the first biased polarity segment 1418 may extend in the depoling direction, while the second biased polarity segment 1419 may extend in the poling direction. The bias signal 1415 may extend for the entire pulse repetition time. For example, the bias signal 1415 may be active during the entire or a desired portion of the repoling period.

The bias signal may be applied i) continuously, ii) only during delivery of the transmit signal, iii) only during delivery of the repoling signal and/or iv) during delivery of both of the transmit signal and the repoling signal. In the foregoing example of FIG. 14 C, the bias signal is shown to have a constant amplitude. Optionally, the bias signal may have varying amplitude. For example, the bias signal may have a first component that is applied contemporaneous with the transmit signals and a second component that is applied contemporaneous with the repoling signals. The first and second components may have constant, but different, voltages. Optionally, the first component may have a constant voltage while the second component has a variable voltage or vice versa.

In accordance with embodiments herein, the repoling signal may have a peak to peak amplitude that is a function of the peak to peak amplitude of the transmit signal. In accordance with some aspects herein, the repoling signal may have an amplitude that is up to 4 times greater than the transmit voltage amplitude, and more preferably, in accordance with other aspects herein, the repoling signal may have an amplitude that is no more than 2.5 times great than the transmit voltage amplitude, and even more preferably no more than 1.5 times greater than the transmit voltage amplitude. In accordance with other aspects herein, the amplitude of the repoling signal may be defined as a raw voltage. For example, the repoling signal may have an amplitude between 40 V and 150 V, more preferably between 70 V and 100 V, and even more preferably between 80 V and 90 V.

In certain embodiments herein, the bias signal, that is applied during the transmit signal, has an amplitude that is a small percentage of the amplitude of the transmit signal. Optionally, the bias signal, that is applied during the repoling signal, may have an amplitude that is the same as or a different percentage of the amplitude of the repoling signal or of the transmit signal For example, the repoling signal may have an amplitude between 40 V and 150 V, more preferably between 70 V and 100 V, and even more preferably between 80 V and 90 V. In connection there with, the bias signal, during repoling, may have an amplitude of up to 50 V, more preferably between 2 V and 25 V and even more preferably between 2 V and 10 V.

For probes with parallel inductors, the repoling pattern may be defined by a series of positive and negative pulses that have a predetermined frequency. The predetermined frequency may be defined based on the type of imaging, the transmit pattern, the receive pattern and the like. For example, the repoling signal may utilize one repoling frequency when performing repoling in connection with transmit cycles for B-mode imaging, and a second repoling frequency when performing repoling in connection with transmit cycles for color Doppler imaging, and yet a third repoling frequency when performing repoling in connection with transmit cycles for pulsed wave Doppler imaging. The repoling frequency may be defined based on, but be different from, the transmit frequency. For example, the frequency for transmit signals generated in connection with one type of ultrasound imaging may be between one and 5 MHz, with a corresponding repoling frequency between 0.5 MHz and 2 MHz, or more preferably between 1 MHz and 2 MHz. As another example, the frequency for transmit signals generated in connection with another type of ultrasound imaging may be between 10 and 15 MHz, with the corresponding repoling frequency between 8 MHz and 10 MHz. Probes without parallel inductors may use any frequency from DC to maximum transmit frequency of the probe.

Figure 14D:
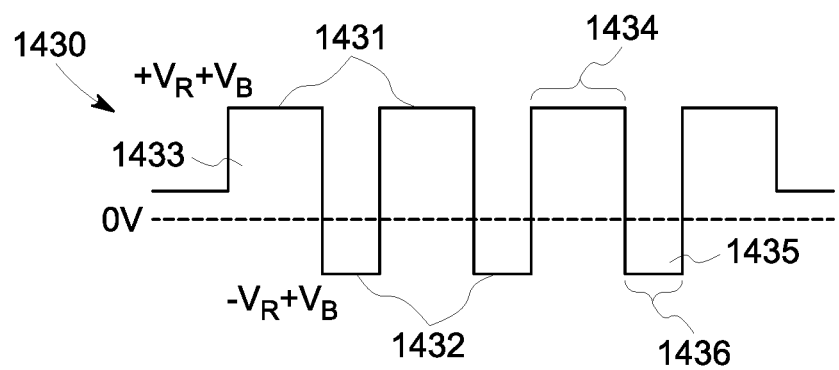
FIG. 14D illustrates an example of a bias repoling signal that may be transmitted during repoling cycles between successive transmit cycles in accordance with embodiments herein.

FIG. 14D illustrates an example of a bias repoling signal 1430 that may be transmitted during repoling cycles between successive transmit cycles (or image frames) in accordance with embodiments herein. The repoling signal 1430 includes a series of pulses having a first polarity segment 1431 (having a positive peak amplitude corresponding to the sum of the peak amplitude of the repoling signal and the peak amplitude of the bias signal) and a series of pulses having a second polarity segment 1432 (having a negative peak amplitude corresponding to the difference between the peak amplitude of the repoling signal and the peak amplitude of the bias signal). The first polarity segment 1431 includes a series of positive pulses 1433 that have a first pulse width 1434. The second polarity segment 1432 includes a series of negative pulses 1435 that have a second different pulse width 1436. In the present example, the positive pulses 1433 have a common pulse duration 1434 that is longer than the pulse duration 1436 of the negative pulses 1435, such as when the poling direction is positive. Alternatively, when the poling direction is negative, the durations of the negative pulses 1435 may be modified to be longer than the durations of the positive pulses 1433.

Figure 14E:
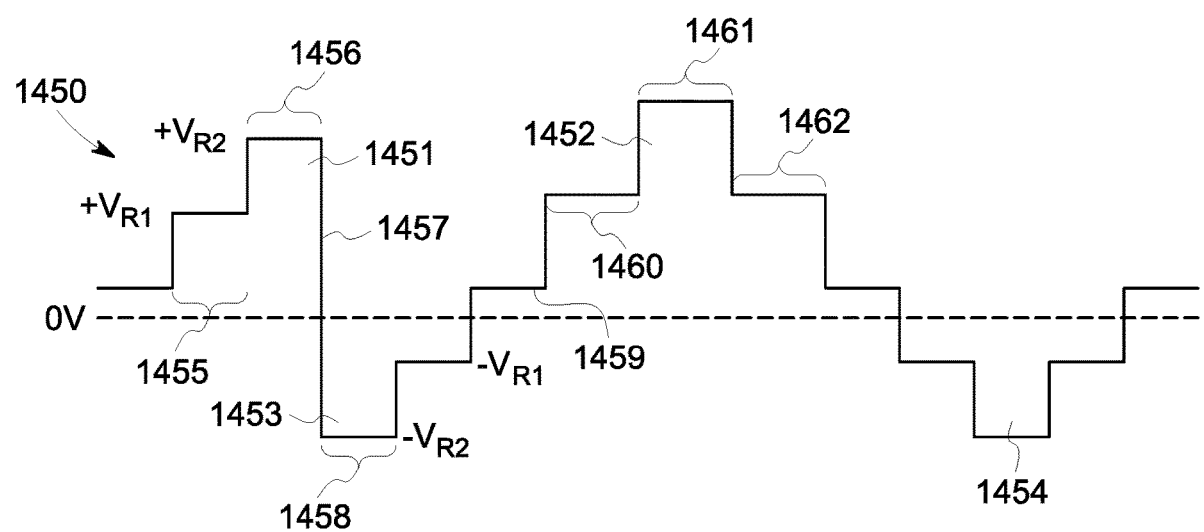
FIG. 14E illustrates an example of an alternative repoling pattern formed in accordance with an embodiment herein.

FIG. 14E illustrates an example of an alternative repoling pattern in accordance with an embodiment herein. A repoling signal 1450 includes a series of positive multistep pulses 1451-1452 and negative multistep pulses 1453-1454. The first positive pulse 1451 includes a first segment with a first amplitude $V_{R1}$ for a duration 1455 and a second segment with a second amplitude $V_{R2}$ for a longer duration 1456. At the end of the first pulse 1451, the repoling signal 1450 transitions at 1457 to the negative pulse 1453 which has a first negative amplitude $^-V_{R2}$ for a first duration 1458, followed by a step down to a lower negative voltage amplitude $^-V_{R1}$ which is maintained for a different duration. The negative pulse 1453 is followed by a short quiescent period 1459 until initiating the next positive pulse 1452 which includes three segments. The first segment includes a first positive voltage amplitude $^+V_{R1}$ maintained for a first duration 1460 followed by a second segment which steps to a higher voltage $^+V_{R2}$ that is maintained for a second duration 1461 until stepping to a third segment which drops back down to the lower positive voltage amplitude $^+V_{R1}$ that is maintained for a third duration 1462. The positive pulse 1452 is followed by a negative pulse 1453 that has a similar stepped shape, but in a negative direction.

Figure 15:
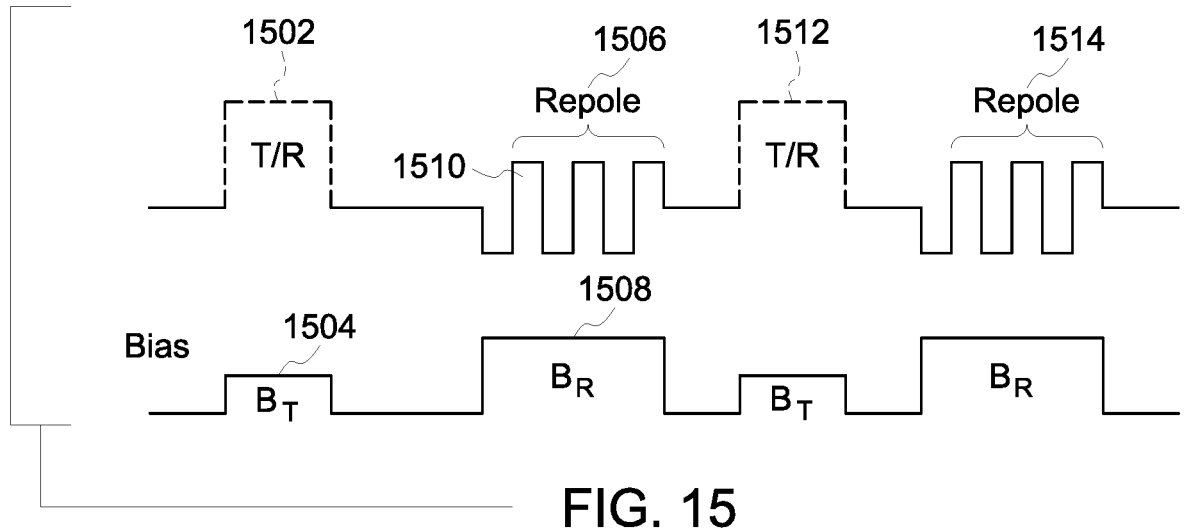
FIG. 15 illustrates an example of a timing relation between transmit cycles and repoling cycles in accordance with an embodiment herein

FIG. 15 illustrates an example of a timing relation between frame transmit cycles and repoling cycles in accordance with an embodiment herein. During a first transmit cycle 1502, one or more transmit signals may be transmitted, followed by related receive operations to collect ultrasound data for part or a complete image frame or 3D data set. During the transmit cycle 1502, a bias signal 1504 is added to each transmit signal as described in connection with various embodiments herein. After completion of the transmit cycle 1502, a repoling cycle 1506 is applied, during which the same or a different bias signal 1508 is added to the repoling signal 1510. The process is repeated for subsequent transmit/receive cycles 1512 and repoling cycles 1514. The repoling cycle 1506 may be implemented in various times, such as at the end of acquisition of an image frame, during a freeze mode, after collecting a 3D data set and the like. FIG. 15 illustrates one example of bias voltages. The bias voltage levels can be implemented in various ways, such as a constant bias voltage, where BT is equal to BR.

In accordance with aspects herein, during the intervals between BT and BR, the voltage level would not be zero. Instead, the voltage for repoling bias signal 1508 would be maintained from the end of the repoling cycle 1506, 1514 until the beginning of the next T/R cycle 1512. Following a T/R cycle the voltage for the transmit bias signal 1504 would be maintained from the end of the T/R cycle 1502, 1512 until the beginning of the next repoling cycle 1506, 1514.

The example of FIG. 15 illustrates one manner in which repoling may be performed in real time during an individual ultrasound scan. In the process of FIG. 15, repoling operations are performed intermittently between transmit/receive scanning operations. Additionally or alternatively, the repoling process may be implemented by ultrasound system separate and apart (and at an entirely different point in time) from any individual ultrasound imaging operation.

Figure 16:
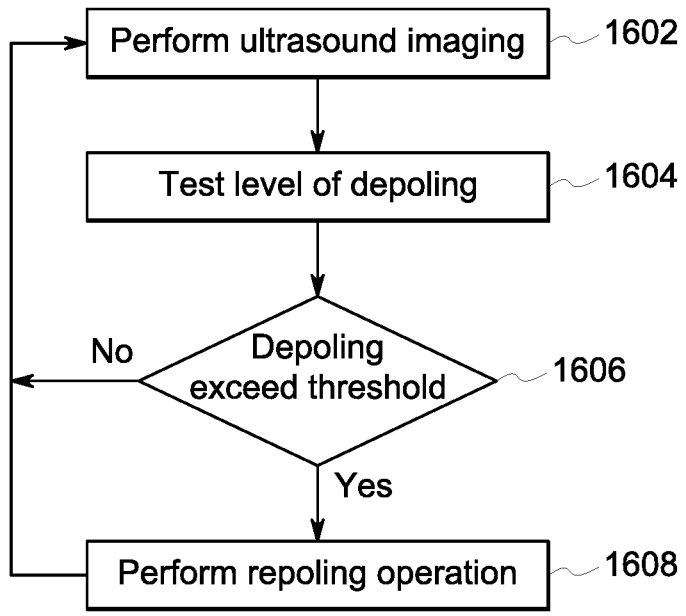
FIG. 16 illustrates a process for implementing repoling in accordance with embodiments herein.

FIG. 16 illustrates a process for implementing repoling in accordance with embodiments herein. At 1602, an ultrasound system is utilized to perform one or more ultrasound imaging operations. The operation at 1602 may include collection of a single ultrasound image (two-dimensional or three-dimensional), or collection of multiple ultrasound images (e.g., in connection with a complete ultrasound examination performed during a clinical visit). Additionally or alternatively, numerous ultrasound examinations may be performed at 1602 over an extended period of time. For example, the operation at 1602 may correspond to a number of days, weeks, months or other period of time. The operation at 1602 may correspond to a number of hours in which an ultrasound system is operated. The operation 1602 may correspond to a number of hours in which an ultrasound probe is utilized, such as when tracking operating time for an individual transducer array.

At 1604, one or more processors of the ultrasound system may perform a test to measure a level of depoling that is exhibited by one or more transducers of the transducer array. For example, the ultrasound system may implement a probe diagnostic analysis that includes, among other things, a measurement of a sensitivity level for one or more transducers within an array. For example, the probe diagnostic analysis may be performed periodically by a technician while holding a probe against a phantom or other probe diagnostic tool. Additionally or alternatively, the ultrasound system may perform the probe diagnostic analysis automatically, such as when a system is being started, at a beginning or end of a patient examination and the like.

The probe diagnostic analysis may measure and record sensitivity levels for the corresponding transducer elements over time. At the time of manufacture or refurbishment, baseline sensitivity levels may be recorded within the memory of the probe and/or ultrasound system, where the baseline sensitivity levels indicate a degree of sensitivity associated with one or more transducer elements that have either no depoling or an extremely small amount of depoling. After periods of use, at 1604, current sensitivity levels are measured.

At 1606, the one or more processors determine whether one or more transducers of a probe exhibit a level of depoling that exceeds a threshold. For example, the one or more processors may determine that the current sensitivity level falls below a predetermined sensitivity level. Additionally or alternatively, the one or more processors may determine that the current sensitivity level has dropped below the baseline sensitivity level by more than a threshold amount (e.g., baseline minus X) and/or more than a threshold percentage (e.g., the current level is at least 30% below the baseline). When the level of depoling does not exceed the threshold, flow returns to 1602 where additional ultrasound imaging operations are performed. Alternatively, when the level of depoling exceeds the threshold, flow moves to 1608.

At 1608, the one or more processors implement a repoling operation by applying a repoling signal (and optionally a bias signal) to the transducer array and/or select transducer elements. By way of example, the processors may generate the repoling signal after at least one of completion of acquisition of ultrasound data for an ultrasound image frame or during a freeze mode. Once the repoling operation is complete, flow returns to 1602 for additional ultrasound imaging operations.

Figure 17:
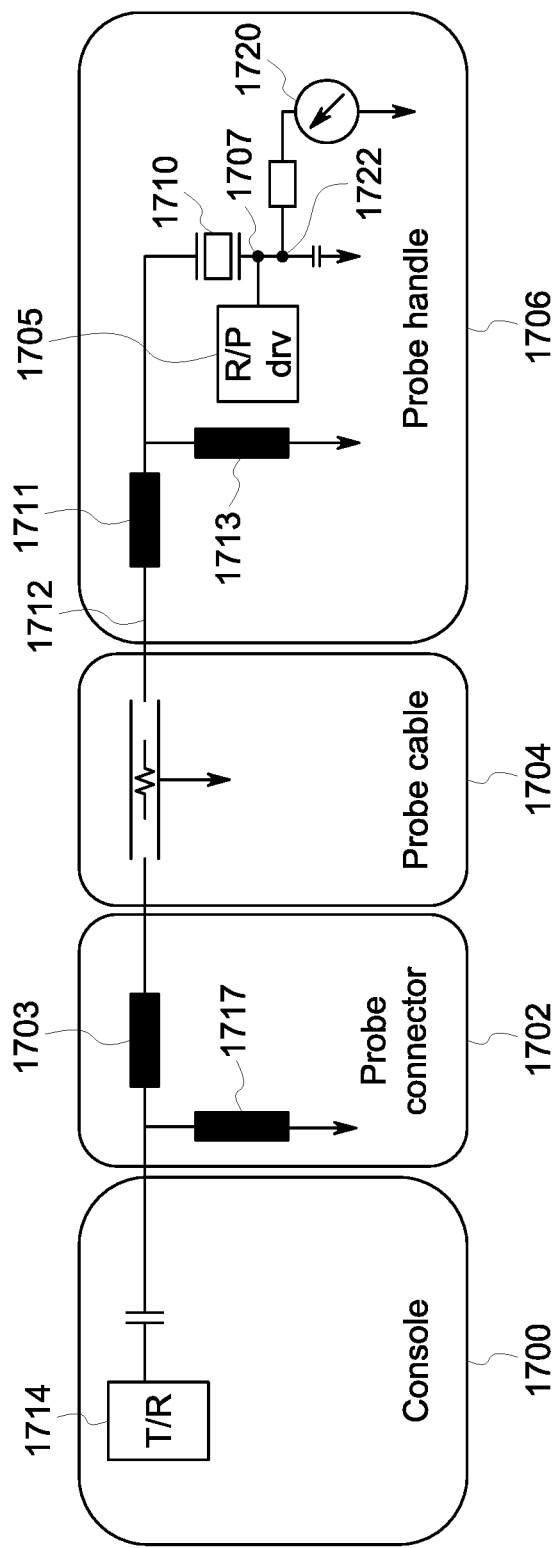
FIG. 17 illustrates a block diagram of an ultrasound system including a DC bias circuit implemented in accordance with embodiments herein.

FIG. 17 illustrates a block diagram of an ultrasound system including a DC bias circuit implemented in accordance with embodiments herein. The ultrasound system includes a console 1700 that is connected to a probe connector 1702. The console 1700 may include all or a portion of the components described and illustrated in connection with one or more of FIGS. 1-4. The probe connector 1702 is provided on a proximal end of a probe cable 1704. A distal end of the probe cable 1704 is connected to a probe 1706. A line 1712 electrically connects a transducer element 1710 to corresponding contacts (not shown) in the probe connector 1702. An inductor combination 1711, 1713 is provided within the probe 1706. An inductor combination 1703 and 1717, within the probe connector 1702, is also provided along line 1712. The probe cable 1704 is connected at the probe connector 1702 to a transmit/receive (T/R) circuit 1714 within the console 1700.

During transmit operations, the T/R circuit 1714 delivers a transmit signal to cause the transducer element 1710 to transmit ultrasound signals. During receive operations, the T/R circuit 1714 records return "echo" signals along line 1712 corresponding to ultrasound echo waves sensed at the transducer element 1710. A biasing circuit 1720 is connected at node 1722 within the probe 1706. The biasing circuit 1720 is configured to introduce a bias signal, such as a DC bias voltage, onto the line 1712. The bias signal is superimposed at node 1722 onto the transmit signal generated by the transmit/receive circuit 1714.

In accordance with new and unique aspects herein, the ultrasound system further includes a repoling drive circuit 1705 provided in the probe handle 1706. The repoling drive circuit 1705 is connected to the transmit line 1712 at node 1707. A single common repoling drive circuit 1705 may be utilized to deliver repoling signals to all of the transducer elements 1710 within the transducer array. Alternatively, a separate repoling drive circuit 1705 may be coupled to each individual transducer elements 1710. Alternatively, a group of repoling drive circuits 1705 may be utilized with a larger group of transducer elements, where each repoling drive circuit 1705 applies a repoling signal to a corresponding subset of transducer elements 1710. The repoling drive circuit 1705 is configured to generate a repoling signal having a repoling pattern configured to at least partially revert the depoling effect exhibited by one or more transducer elements. The configuration of FIG. 17 allows the biasing circuit 1720 and repoling circuit 1705 to be implemented within each individual probe 1706, thereby avoiding any need for modification to conventional consoles for ultrasound systems.

In the embodiment of FIG. 17, the inductors 1713, 1717 are provided in parallel with the repoling drive circuit 1705 and may be configured to apply a voltage "over-boosting" operation. During the voltage over-boost, when a pulse of the repoling signal is initially applied, the pulse charges the inductors. During a next pulse of the repoling signal, the charge stored in the inductor is applied to one side of the transducer element, while the repoling drive circuit 1705 delivers the next pulse to the opposite side of the transducer element, thereby boosting a voltage potential experienced across the transducer element based on the combination of the charge stored in the inductors and the charge delivered by the repoling drive circuit. By utilizing inductors to form an over boosting circuit, embodiments herein reduce the maximum voltage that needs to be delivered by the repoling drive circuit. For example, if the repoling drive circuit is designed to deliver a maximum voltage of +/−40 V, and the inductor(s) 1713, 1717 are designed to create a voltage over boost of 20V, a resulting potential applied across the transducer element would shift between maximum positive and negative voltages of +60V to −40V.

Optionally, the embodiment of FIG. 17 (as well as other embodiments herein) may be implemented in connection with wireless probes where the bias circuitry and repoling circuitry is implemented within the probe handle.

Figure 18:
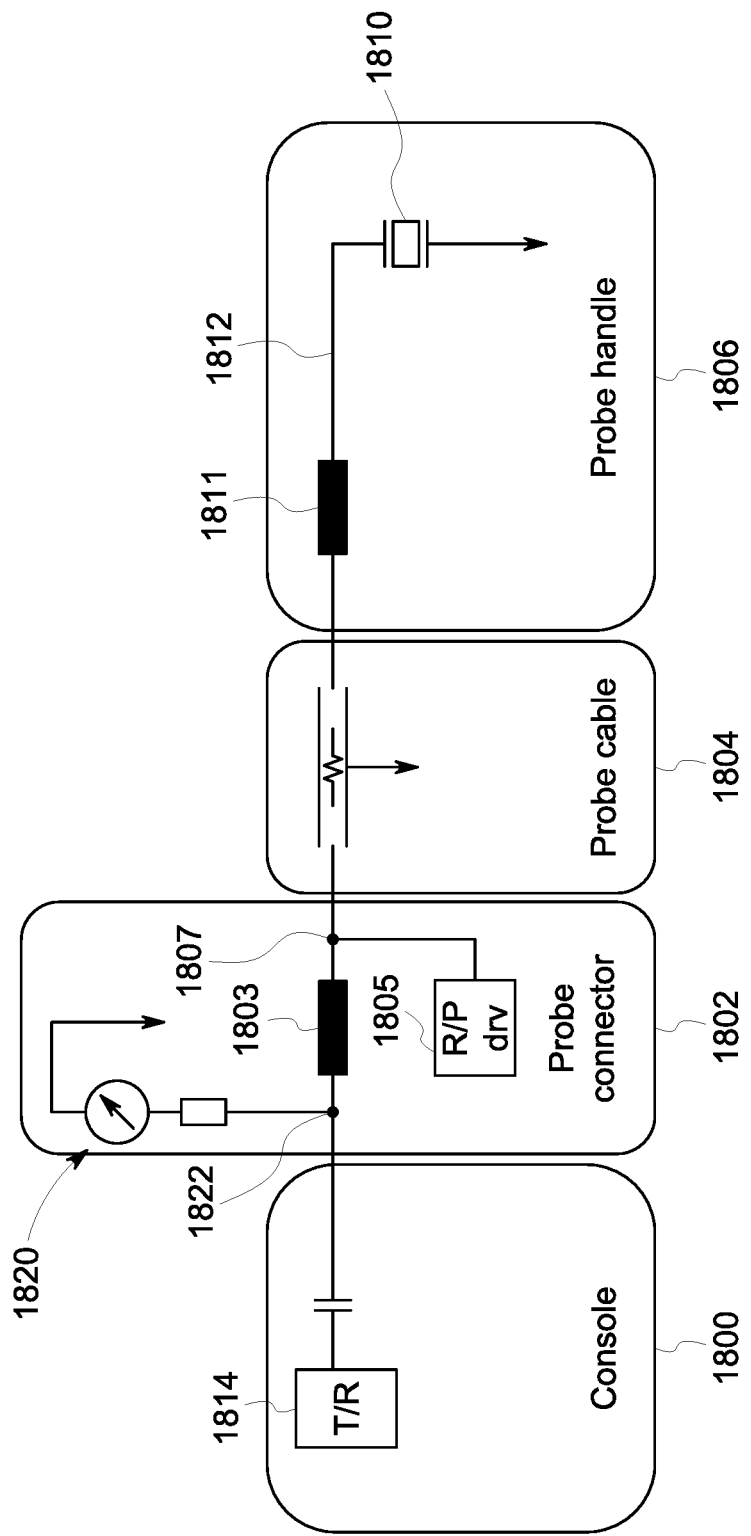
FIG. 18 illustrates a block diagram of an ultrasound system including a DC bias circuit implemented in accordance with embodiments herein.

FIG. 18 illustrates a block diagram of an ultrasound system including a DC bias circuit implemented in accordance with embodiments herein. The ultrasound system includes a console 1800 that is connected to a probe connector 1802. The console 1800 may include all or a portion of the components described and illustrated in connection with one or more of FIGS. 1-4. The probe connector 1802 is provided on a proximal end of a probe cable 1804. A distal end of the probe cable 1804 is connected to a probe 1806. A line 1812 electrically connects a transducer element 1810 to corresponding contacts (not shown) in the probe connector 1802. An inductor 1811 is provided within the probe 1806, and an inductor 1803 is provided within the probe connector 1802 along line 1812. The probe cable 1804 is connected at the probe connector 1802 to a transmit/receive (T/R) circuit 1814 within the console 1800. The inductors 1803 and 1811 are optional and the connection 1807 and 1822 could be on both sides of the inductor.

During transmit operations, the T/R circuit 1814 delivers a transmit signal to cause the transducer element 1810 to transmit ultrasound signals. During receive operations, the T/R circuit 1814 records return "echo" signals along line 1812 corresponding to ultrasound echo waves sensed at the transducer element 1810. A biasing circuit 1820 is connected at node 1822 within the probe connector 1802. The biasing circuit 1820 is configured to introduce a bias signal, such as a DC bias voltage, onto the line 1812. The bias signal is superimposed at node 1822 onto the transmit and receive line. In accordance with new and unique aspects herein, the ultrasound system further includes a repoling drive circuit 1805 provided in the probe connector 1802. The repoling drive circuit 1805 is connected to the transmit line 1812 at node 1807. It is understood that a single common repoling drive circuit 1805 may be utilized to deliver repoling signals to all of the transducer elements 1810 within the transducer array. Alternatively, a separate repoling drive circuit 1805 may be coupled to each individual transducer elements 1810. Alternatively, a group of repoling drive circuits 1805 may be utilized with a larger group of transducer elements, where each repoling drive circuit 1805 applies a repoling signal to a corresponding subset of transducer elements 1810. The repoling drive circuit 1805 is configured to generate a repoling signal having a repoling pattern configured to at least partially revert the depoling effect exhibited by one or more transducer elements. The configuration of FIG. 18 allows the biasing circuit 1820 and repoling circuit 1805 to be implemented within the probe connector 1802, thereby avoiding any need for modification to conventional consoles for ultrasound systems and potentially to an existing design for the internal components of the probe body.

CLOSING STATEMENTS

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

Aspects are described herein with reference to the Figures, which illustrate example methods, devices and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. An ultrasound system, comprising:
a transducer with piezoelectric transducer elements formed from a slab of piezoelectric material and polarized in a poling direction, wherein over time one or more of the piezoelectric transducer elements exhibit a depoling effect; and
one or more drive circuits configured to:
  generate a repoling signal having a repoling pattern configured to at least partially revert the depoling effect exhibited by the one or more piezoelectric transducer elements; and
  generate a bias signal in the poling direction, wherein the bias signal is combined with the repoling signal to form a biased repoling signal, that is shifted in the poling direction.

2. The ultrasound system of claim 1, wherein the one or more drive circuits are further configured to generate a transmit signal having at least first polarity segments, the first polarity segments having corresponding first peak amplitudes, wherein the bias signal is combined with the transmit signal to form a biased transmit signal, that is shifted in the poling direction.

3. The ultrasound system of claim 1, wherein the one or more drive circuits are configured to generate the bias signal contemporaneous in time with the repoling signal.

4. The ultrasound system of claim 2, wherein the one or more drive circuits include a transmit drive circuit configured to generate the transmit signal.

5. The ultrasound system of claim 1, wherein the one or more drive circuits include a repoling drive circuit configured to generate the repoling signal.

6. The ultrasound system of claim 2, wherein the one or more drive circuits include at least one common drive circuit configured to generate at least two of the transmit signal, the bias signal, and the repoling signal.

7. The ultrasound system of claim 1, wherein the one or more drive circuits are configured to generate, as the repoling signal, a series of at least one positive pulse and at least one negative pulse.

8. The ultrasound system of claim 2, wherein the one or more drive circuits are configured to generate the repoling signal to have a voltage amplitude of up to 4 times greater than a voltage amplitude of the transmit signal.

9. An ultrasound probe, comprising:
a transducer with piezoelectric transducer elements formed from a slab of piezoelectric material and polarized in a poling direction, wherein over time one or more of the piezoelectric transducer elements exhibit a depoling effect;
a probe connector and a transmit line extending from the probe connector to the transducer, the transmit line configured to convey a transmit signal having at least first polarity segments, the first polarity segments having corresponding first peak amplitudes;
the transmit line further configured to convey a repoling signal having a repoling pattern configured to at least partially revert the depoling effect exhibited by the one or more piezoelectric transducer elements; and
a bias generator configured to generate a bias signal in a direction of the poling direction, the bias signal combined with the transmit signal to form a biased transmit signal that is shifted in the poling direction and still includes both of positive and negative voltages over a transmit cycle, the bias signal combined with the repoling signal to form a biased repoling signal that is shifted in the poling direction.

10. The ultrasound probe of claim 9, wherein the bias generator is configured to generate the bias signal contemporaneous in time with the repoling signal.

11. The ultrasound probe of claim 9, further comprising a repoling drive circuit within a housing of the ultrasound probe, the repoling drive circuit configured to generate the repoling signal.

12. The ultrasound probe of claim 9, wherein the repoling signal includes a series of at least one positive pulse and at least one negative pulse.

13. The ultrasound probe of claim 9, wherein the repoling signal has a voltage amplitude of up to 4 times greater than a voltage amplitude of the transmit signal.

14. A method, comprising:

utilizing a transducer to transmit ultrasound signals and receive echo ultrasound signals from a region of interest, the transducer including piezoelectric transducer elements formed from a slab of piezoelectric material and polarized in a poling direction, wherein over time one or more of the piezoelectric transducer elements exhibit a depoling effect;

generating a repoling signal having a repoling pattern configured to at least partially revert the depoling effect exhibited by the one or more piezoelectric transducer elements; and generating a bias signal in the poling direction, the bias signal combined with the repoling signal to form a biased repoling signal, that is shifted in the poling direction.

15. The method of claim 14, further comprising generating a transmit signal having at least first polarity segments, the first polarity segments having corresponding first peak amplitudes, wherein the bias signal is combined with the transmit signal to form a biased transmit signal, that is shifted in the poling direction.

16. The method of claim 14, wherein the generating the bias signal comprises generating the bias signal contemporaneous in time with the repoling signal.

17. The method of claim 14, further comprising generating the repoling signal after at least one of completion of acquisition of ultrasound data for an ultrasound image frame or during a freeze mode.

18. The method of claim 14, wherein the repoling signal comprises a series of at least one positive pulse and at least one negative pulse.

19. The method of claim 15, wherein the repoling signal has a voltage amplitude of up to 4 times greater than a voltage amplitude of the transmit signal.

20. The method of claim 15, further comprising continuously applying a DC voltage as the bias signal to both the transmit signal and the repoling signal.

* * * * *